US005788957A

United States Patent [19]

Harris

[11] Patent Number: 5,788,957
[45] Date of Patent: *Aug. 4, 1998

[54] ENZYME-ORTHOKERATOLOGY

[75] Inventor: Donald H. Harris, Laguna Niguel, Calif.

[73] Assignee: Advanced Corneal Systems, Inc., Irvine, Calif.

[*] Notice: The term of this patent shall not extend beyond the expiration date of Pat. Nos. 5,270,051 and 5,626,865.

[21] Appl. No.: 712,967

[22] Filed: Sep. 12, 1996

Related U.S. Application Data

[63] Continuation of Ser. No. 211,749, Jul. 18, 1994, Pat. No. 5,626,865, which is a continuation-in-part of Ser. No. 776, 211, Oct. 15, 1991, Pat. No. 5,270,051.

[51] Int. Cl.[6] .................... A61F 2/14; A61K 37/54; C12N 9/26; C12N 11/08

[52] U.S. Cl. .................. 424/78.04; 424/94.62; 424/423; 424/427; 424/428; 424/429; 514/912; 435/180; 435/185; 435/201; 623/4; 623/5

[58] Field of Search .................. 424/94.62, 28.08, 424/423, 427, 428, 429; 514/912; 435/108, 182, 201; 623/4, 5

[56] References Cited

U.S. PATENT DOCUMENTS

| | | | |
|---|---|---|---|
| 1,929,228 | 10/1933 | Wilhelm | 351/160 R |
| 3,302,646 | 2/1967 | Behney | 424/429 |
| 3,416,530 | 12/1968 | Ness | 424/427 |
| 3,485,244 | 12/1969 | Rosen | 424/429 |
| 3,710,796 | 1/1973 | Neefe | 424/429 |
| 3,760,807 | 9/1973 | Neefe | 424/429 |
| 3,776,230 | 12/1973 | Neefe | 604/291 |
| 3,786,812 | 1/1974 | Neefe | 424/429 |
| 3,831,604 | 8/1974 | Neefe | 424/429 |
| 3,957,049 | 5/1976 | Neefe | 424/429 |
| 4,174,389 | 11/1979 | Cope | 424/94 |
| 4,484,922 | 11/1984 | Rosenwald | 424/429 |
| 4,540,417 | 9/1985 | Poler | 424/429 |
| 4,571,039 | 2/1986 | Poler | 424/429 |
| 4,592,752 | 6/1986 | Neefe | 424/429 |
| 4,902,692 | 2/1990 | Chan | 514/299 |
| 5,270,051 | 12/1993 | Harris | 424/429 |

FOREIGN PATENT DOCUMENTS

| | | |
|---|---|---|
| 861753 | 1/1953 | German Dem. Rep. . |
| 2308144 | 8/1974 | German Dem. Rep. . |
| 2426757 | 12/1975 | German Dem. Rep. . |

OTHER PUBLICATIONS

Wyeth Laboratories Inc. Wyeth® Wydase® (Hyaluronidase): May 14, 1987.

Chiron Ophthalmics, Medilens™ Corneal Shield: Jun. 1990.

Charles Harrison May, O.D. FAAO, FIOS Basic Orthokeratology Computerized© 1990.

Chiron Ophthalmics Medlines™ Monograph; Undated.

Physician's Desk Reference Product Information Wydase® (Hyaluronidase) Injection: pp. 2214–2215; Undated.

Chiron Ophthalmics Medilens™ Monograph; Undated.

Physician's Desk Reference Information Wydase® (Hyaluronidase).

Donald Hughes Harris, Corneal Changes in Myopia Reduction, Orthokeratology, vol. IV, 1978.

Donald Hughes Harris, Accommdate Convergence Control in Myopia Reduction: American Optometric Association Journal, vol. 45, No. 3, Mar. 1974.

Donald Hughes Harris, Research Results of 160 Eye Study: National Eye Research Foundation, Oct. 1990.

Donald Hughes Harris, Orthokeratology Myopia Control: Newport Beach Optometric Eyecare Center, Undated.

Triester, et al., Effect of Hyaluronidase: Arch. Opthal., vol. 81, pp. 647–649, May 1969.

*Primary Examiner*—Frederick Krass
*Attorney, Agent, or Firm*—Knobbe, Martens, Olson & Bear, LLP

[57] ABSTRACT

A method and apparatus for correcting refractive errors of the eye are disclosed. Accelerated reshaping of the corneal tissue is accomplished by administering one or more enzymes and/or other agents to the eye which temporarily soften the cornea. The cornea is thereafter fitted with a rigid contact lens or a series of lenses which have a concave curvature that will correct a refractive error. The softened cornea then rapidly reshapes its convex curvature to the concave curvature of the contact lens or series of lenses, thereby rendering the eye emmetropic. The enzymes and/or other agents then dissipate from the cornea, and the cornea "hardens" to retain the new emmetropic shape. After "hardening" has occurred, the lens rendering the eye emmetropic is removed.

29 Claims, 11 Drawing Sheets

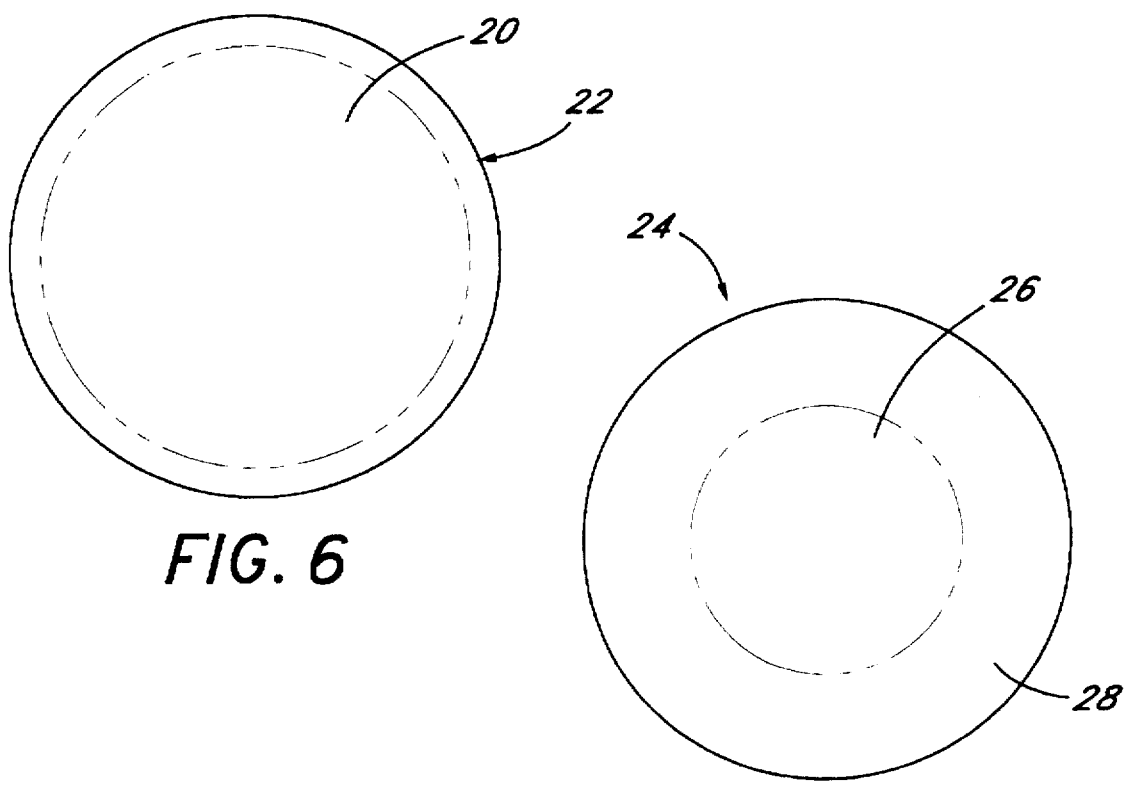
FIG. 6
FIG. 7
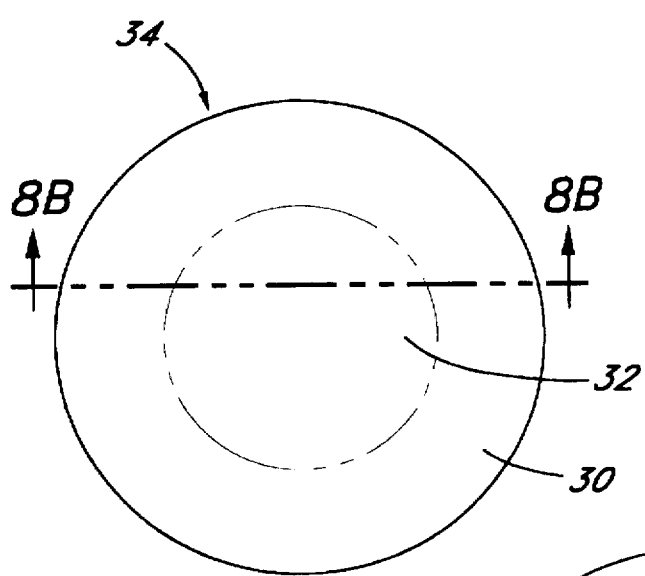
FIG. 8A
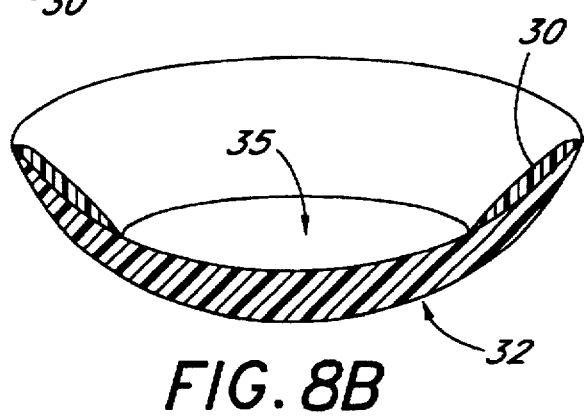
FIG. 8B

ENZYME-ORTHOKERATOLOGY

This application is a continuation of U.S. patent application Ser. No. 08/211,749, filed on Jul. 18, 1994, now U.S. Pat. No. 5,626,865 which is a continuation-in-part of U.S. patent application Ser. No. 07/776,211, filed Oct. 15, 1991, now issued as U.S. Pat. No. 5,270,051.

FIELD OF THE INVENTION

The present invention relates to apparatuses and methods for accelerated corneal reshaping involving the release of enzyme(s) or other agents which facilitate reshaping of the cornea to reduce or eliminate refractive errors of the eye.

BACKGROUND OF THE INVENTION

Approximately eighty percent of the refracting power of the eye is at the cornea. When the cornea is misshapen or the axial length of the eye is too long or too short, or when the lens of the eye is functioning abnormally, the refractive errors of myopia, astigmatism or hyperopia can result. Spectacles correct refractive errors by refracting the light with a lens before it reaches the cornea in order to change the angle at which light enters the cornea. Contact lenses correct refractive errors of the eye by replacing the misshapen cornea with the front curve of a contact lens which is calculated to render the eye emmetropic (a state where no visual correction is necessary). When the lens is taken off, however, the cornea is still misshapen or defective and refractive errors still exist.

The cornea itself is composed of five layers. The outermost layer is the epithelium, which is 4–5 cells thick. Beneath the epithelium is the acellular Bowmans membrane. The middle layer is the stroma, which is composed of scattered corneal fibroblasts (keratocytes) among organized lamellae of collagen, proteoglycans, and glycoproteins. Below the stroma is another acellular layer called Descemet's membrane. The innermost layer of the cornea, comprised of a single layer of flattened cells, is the endothelium.

The structural components of the human cornea are chiefly proteoglycans and collagens. Proteoglycans are composed of a hyaluronate core, a protein core, and glycosaminoglycans, which are proteoglycan monomers with repeating disaccharide units. Approximately 60% of the glycosaminoglycans of the cornea are made up of keratan sulfate, while the remaining 40% are mostly chondroitin sulfate. The other main structural component of the cornea, collagen, is found in seven different forms in the human cornea.

These structural components of the cornea are somewhat pliable and allow the cornea to be reshaped with a series of progressive contact lens changes to correct refractive errors. This procedure is known as Orthokeratology. The methods of Orthokeratology without the use of enzymes or other agents originated in 1962 as an extension of normal contact lens use. Orthokeratology is generally defined as the therapeutic use of contact-lenses to reshape the corneal curvature, thereby improving refractive errors of the eye. Dr. Charles May and Dr. Stuart Grant are credited with pioneering the process. University and clinical level research over the next 20 years has confirmed the safety, effectiveness, and retention of this procedure. Orthokeratology has today become a contact lens specialty practice for a limited number of private practitioners, primarily in the United States.

Traditional Orthokeratology procedures use a series of progressive contact lens changes to reshape the cornea, thereby producing a cornea with a more spherical shape. This reduces or eliminates myopia and astigmatism and improves natural vision. Once a desired corneal curvature has been produced, retainer contact lenses are worn to stabilize the results. The contact lenses are made of a rigid gas permeable material and contain no enzymes or agents. The length of a program of treatment varies from six to eighteen months with progressive contact lens changes and examinations every two to six weeks.

A common fitting formula for Orthokeratology is as follows:

Lens Base Curve In Diopters=Flattest central corneal curvature in diopters to 1.0 diopter flatter.

Lens Diameter=Base curve in mm+1.5 mm $$\text{Power} = \text{Subjective } \underline{RX} \pm \frac{\text{Base Curve}}{\text{Central Curvature}} \text{ relationship}$$

Thickness=0.18 mm for 0 power—subtract 0.01 mm for each 1 diopter minus; add 0.02 mm for each 1 diopter of plus Intermediate Curve=Base Curve in mm+1.5 mm, width= 0.35–0.5 mm Peripheral Curve=Base Curve in mm+3.0 mm, width= 0.35–0.5 mm When treating myopia, new contact lenses are refit with flatter curvatures, less correction, larger diameters, and greater thickness as the Orthokeratology program progresses. The patient's central corneal curvature continues to lessen (flatten and become more spherical), myopia and astigmatism are reduced, and unaided (natural) visual acuity improves significantly. When the maximum desired results are achieved or the patient ceases to improve, retainer contact lenses are worn full time or part time to retain the results.

For traditional Orthokeratology procedures, university and clinical research indicates the following limits of change: 4 diopters of myopia and 2.5 diopters of astigmatism change, no appreciable hyperopia change, 2 diopters of central corneal change, and 9 lines of unaided visual acuity change on the Snellen chart. Regression may occur in hours or days if retainer lenses are not worn.

Notwithstanding the foregoing, there remains a need for an improved method of correcting refractive errors in the eye nonsurgically which can correct larger degrees of refractive error and produce relatively permanent results in a much shorter period of time.

SUMMARY OF THE INVENTION

The first aspect of the present invention provides a contact lens for delivering agents to an eye. The lens includes a rigid anterior layer and a rigid posterior layer. The convex side of the posterior layer has a flatter curvature than the concave side of the anterior layer over a center portion of the posterior layer. The lens also includes a channel in the center portion of the posterior layer. The channel passes from the convex side of the posterior layer to the concave side of the posterior layer. The concave side of the anterior layer and the convex side of the posterior layer are joined, thereby forming a center chamber between the layers in communication with the concave side of the posterior layer by means of the channel. In a preferred form in this aspect of the invention, the concave side of the posterior layer has a curvature sufficient to produce emmetropia in an eye.

The second aspect of the present invention also provides a contact lens for delivering agents to an eye. The contact lens of this aspect also includes a rigid anterior layer and a rigid posterior layer. In this aspect, an intermediate portion of the posterior surface of the anterior layer has a steeper radius of curvature than the anterior surface of an intermediate portion of the posterior layer. The lens of this aspect has a channel in the intermediate portion of the posterior layer. The channel passes from the convex side of the posterior layer to the concave side of the posterior layer. The concave side of the anterior layer and the convex side of the posterior layer are joined, thereby forming a peripheral chamber between the layers in the intermediate portions. The channel is in communication with both the peripheral chamber and the posterior surface of the posterior layer of the contact lens. In a preferred embodiment of this aspect of the invention, the concave side of the posterior layer has a central radius of curvature sufficient to produce emmetropia in the eye. Still another aspect of the present invention provides an agent that softens the cornea of a mammalian eye for use in correcting refractive errors in the mammalian eye. The agent can be provided in combination with a rigid contact lens. The contact lens in the combination preferably has a concave curvature to produce a desired configuration in the eye.

In yet another aspect of the present invention, there is provided a method of reshaping a cornea from a first configuration to a second desired configuration in order to correct refractive errors in an eye of a subject mammal. In this method a soft contact lens is provided and loaded with an amount of a corneal softening agent sufficient to soften the cornea in the eye. Thereafter, soft contact lens is fitted to the cornea and the softening agent in the soft contact lens causes the cornea to become softer and more pliable. This is followed by removing the soft contact lens and fitting at least one rigid contact lens to the cornea while the cornea is in the softened condition, thereby causing the cornea to reshape to the configuration of the concave curvature of the rigid contact lens. In a preferred form of this method, the soft contact lens comprises a hydrophilic material, such as collagen. The soft contact lens can be loaded with the corneal softening agent by soaking the soft contact lens in a solution of the agent. In one preferred form of this method, a rigid retainer contact lens is fitted on top of the soft contact lens while the soft contact lens is on the cornea to maintain the shape of the cornea during the softening process. In this preferred form, it is more preferable for the soft contact lens to be bonded to the rigid retainer contact lens. In another preferred form of the method, the method includes administering to the eye an amount of an inhibitor of the agent sufficient to slow or stop the softening activity of the agent. Thus, in this preferred form of the method, the inhibitor is added after the cornea has softened and reshaped to the desired second configuration. The the inhibitor can be a metalloproteinase inhibitor, such as EDTA, N-ethylmalimine, cycloheximide, 1,10 phenantroline, phenylmethane sulfonyl fluoride, TIMP, TIMP-2, or IMP. The inhibitor can also be a collagenase inhibitor, such as compounds containing ferric ($Fe^{2+}$) ions or compounds containing cupric ($Cu^{2+}$) ions. Another possible inhibitor is cysteine.

In another aspect of the present invention, a method of correcting refractive errors in an eye of a subject mammal is disclosed, comprising the step of first administering to the subject a corneal softening amount of an agent that softens the cornea in the eye of the subject so that the cornea can be reshaped from a first configuration to a desired second configuration. After the cornea has been softened, a rigid contact lens having a concave curvature of the desired second configuration is fit onto the cornea. Under the influence of the lens, the cornea is permitted to reshape to the desired second configuration. When the cornea is capable of maintaining the desired second configuration without the support of the lens, the lens is removed. The corneal softening agent can be chosen from any of a number of enzymes, enzyme activators, and other agents which act on the structural components of a cornea. For example, the corneal softening can be an enzyme which breaks down proteoglycans in the cornea, such as chondroitinase AC, chondroitinase ABC, keratanase, hyaluronidase, or matrix metalloproteinase-3. Such an agent can also be an enzyme which breaks down collagen in the cornea, such as matrix metalloproteinase-1 or matrix metalloproteinase-2. In another embodiment, the agent is an activator of an endogenous enzyme which breaks down structural components of the cornea. Such an agent can be, for example, an activator of an endogenous metalloproteinase enzyme such as interleukin-1, interleukin-1α, tumor necrosis factor, monosodium urate monohydrate, 4-amino phenylmercuric acetate, human serum amyloid A, human $B_2$ microglobin, and copper chloride. In yet a further embodiment, the corneal softening agent used in the present methods of Enzyme-Orthokeratology can be an inactivator which inactivates an inhibitor of an endogenous enzyme. Such an inactivator can be, for example, iodoacetamide. In a preferred embodiment, the foregoing corneal softening agents can be administered in combination with an anaesthetic such as proparacaine hydrochloride in order to minimize any discomfort associated with the administration of such agents. The agent can be administered in the form of eye drops. The the eye drops can include liposomes which contain the agent. The agent can also be administered to the cornea by means of iontophoresis. Preferably, the rigid contact lens carries an amount of the agent sufficient to soften the cornea and the agent is administered to the eye by means of the rigid contact lens. In a preferred form of this method, the rigid contact lens includes a chamber between the anterior and posterior surfaces thereof and a hole in the posterior surface thereof. In this preferred form, the agent is released from the chamber and through the hole. A series of rigid contact lenses containing the agent in the chamber can be successively fitted to the cornea with the central concave radius of the posterior surface of each successive lens being progressively more similar to that of a desired corneal configuration. In another preferred form, the contact lens can be constructed from two layers laminated to each other. In this preferred form, a chamber for holding fluid is formed between the two layers when the contacting surfaces of the two layers are laminated together. The posterior layer of the contact lens used in this preferred form has at least one hole for delivering fluid from the chamber to the eye. The central concave radius of the contact lens can be equal to the convex radius required by the cornea to render the eye emmetropic. The agent can also be administered by injecting the agent directly into the corneal stroma from a side of the eye or by injecting the agent anteriorly through the epithelium of the eye. The method can also include fitting a soft contact lens which comprises a material, such as collagen, that is impregnated with the agent before fitting the rigid contact lens. This method can be used with inhibitors which slow or halt the corneal softening activity of agents used in the present method to soften a cornea. Such agents aid in the hardening of a cornea after it has been softened and help to lock in a desired configuration which has been imparted to the cornea. Promoting such corneal hardening involves administering to the eye of a subject whose cornea has been softened with a corneal softening agent an amount of an inhibitor of the agent sufficient to slow or stop the softening activity of the agent. Such an inhibitor is added after the cornea has been softened and reshaped to a desired configuration. The inhibitor can be, for example, a metalloproteinase inhibitor such as EDTA, N-ethylmalimine, cycloheximide, 1,10 phenantroline, phenylmethane sulfonyl fluoride, TIMP, TIMP-2, or IMP. Such an inhibitor can also be a collagenase inhibitor such as a compound containing a ferric ($Fe^{2+}$) ion or a compound containing cupric ($Cu^{2+}$) ion. Where the corneal softening agent used is hyaluronidase, the inhibitor can be a hyaluronidase inhibitor such as cysteine and EDTA.

Another aspect of the present invention provides a method of correcting refractive errors in an eye of a subject mammal. The method includes the step of providing a combination contact lens having a rigid center and a soft annular skirt extending beyond the outer perimeter of the rigid center. The rigid center has a paracentral curvature sufficient to render an eye of the subject mammal emmetropic. Another step of this method is loading the annular skirt with an amount of a cornea softening agent sufficient to soften the cornea of the eye, releasing the cornea softening agent into the cornea, thereby softening the cornea and making it more pliable. Then, the cornea is reshaped to the posterior curvature of the rigid center of the combination lens and rendering the eye emmetropic.

The invention also provides another aspect that is a method of correcting refractive errors in an eye of a subject mammal. This method includes the step of providing the contact lens as described above as the first aspect of the present invention. The center chamber of the contact lens portion is loaded with an amount of a corneal softening agent sufficient to soften the cornea of the eye. This agent is released into the cornea from the central chamber, thereby softening the cornea and making it more pliable, the cornea then reshaping to the inside central curvature of the posterior layer of the contact lens.

Still another aspect of the invention is also a method of correcting refractive errors in an eye of a subject mammal. In this method, a contact lens as described as the second aspect of the present invention is provided. The method includes the step of loading the peripheral chamber of the contact lens with an amount of a corneal softening agent sufficient to soften the cornea of the eye. The corneal softening agent is released into the cornea from the central chamber, thereby softening the cornea and making it more pliable, the cornea then reshaping to the inside central curvature of the posterior layer.

The invention also includes another aspect in which there is provided a method of rehabilitating corneal irregularity and correcting refractive error in an eye of a subject mammal with irregular corneal shape. This method includes the step of identifying a subject with irregular corneal shape. A corneal softening amount of an agent that softens the cornea of the eye of the subject is administered to the subject so that the cornea can be reshaped from a first configuration to a desired second configuration. The cornea is then fitted with a contact lens having a concave curvature of the desired second configuration and the cornea permitted to reshape to the desired second configuration under the influence of the lens. The lens is removed when the cornea is capable of maintaining the desired second configuration without the support of the lens. The subject can be identified by diagnosing the subject as having one of the following conditions keratoconus, contact lens induced corneal warpage, irregular corneal shape or uncorrected refractive error due to corneal surgery.

In yet another aspect, there is provided a method of improving the clinical success of surgery to the eye involving the manipulation of a cornea of a subject mammal. This method includes identifying a subject who has undergone a corneal manipulation and administering to the subject a corneal softening amount of an agent that softens a manipulated cornea of the subject so that the cornea can be reshaped from a first configuration to a desired second configuration. The cornea is fitted with a contact lens having a concave curvature of the desired second configuration and the cornea permitted to reshape to the desired second configuration under the influence of the lens. The lens is removed when the cornea is capable of maintaining the desired second configuration without the support of the lens. The corneal manipulation can be any of a variety of such techniques, including radial keratotomy, corneal transplant surgery, cataract surgery, and corneal reshaping by laser.

The invention also includes a method of slowing or halting the softening of a cornea and promoting corneal hardness. This method includes the administration of a corneal hardening amount of an inhibitor of an enzyme or agent which produces corneal softening. Any of a variety of inhibitors can be used, including EDTA, N-ethylmalimine, cycloheximide, 1,10 phenantroline, phenylmethane sulfonyl fluoride, TIMP, TIMP-2, IMP, cysteine, ferric ion, and cupric ion.

BRIEF DESCRIPTION OF THE DRAWINGS

FIG. 6 is a plan view of an enzyme releasing soft collagen contact lens.

FIG. 7 is a plan view of a saturn-type enzyme releasing lens.

FIG. 8A is a plan view of a "piggy back" enzyme releasing Orthokeratology lens.

FIG. 8B is a cross-sectional view taken along the lines 8b—8b in FIG. 8a.

FIG. 10B is an enlarged schematic view of the components of the corneal stroma encompassed by circle 10b of FIG. 10a.

DETAILED DESCRIPTION OF PREFERRED EMBODIMENTS

Figure 10:
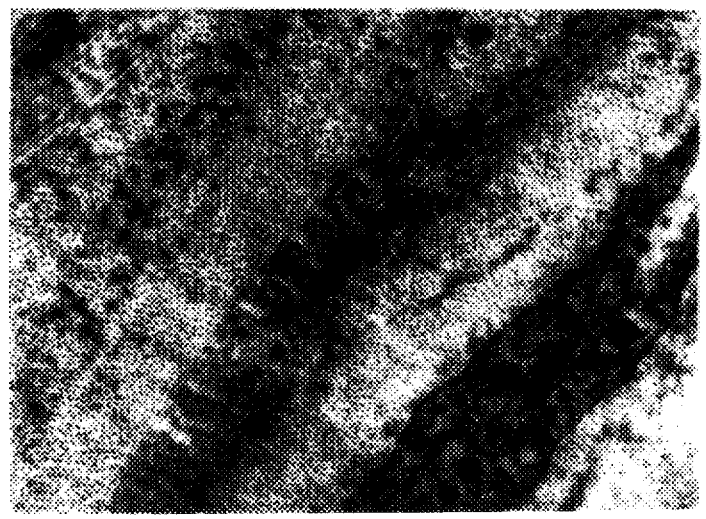
FIG. 10 is an enlargement of the microphotograph illustrating the human stroma (collagen fibrils and mucopolysaccharide layers).
Figure 10A:
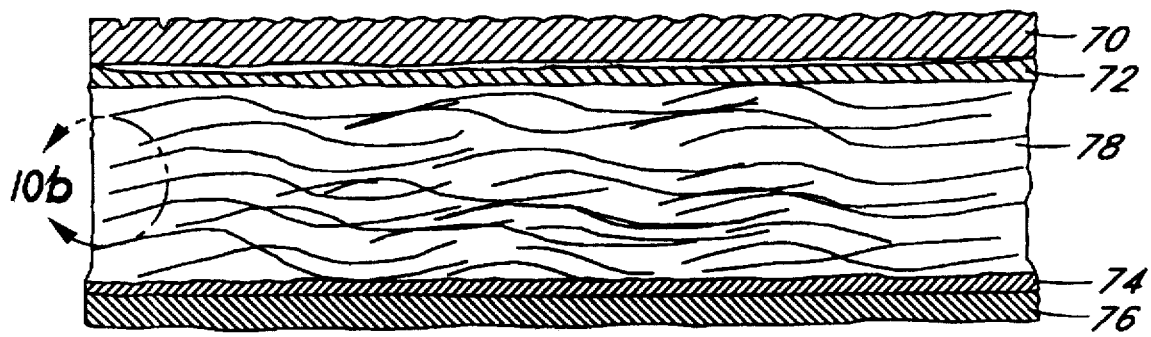
FIG. 10A is a schematic diagram showing a cross section of a human cornea.
Figure 10B:
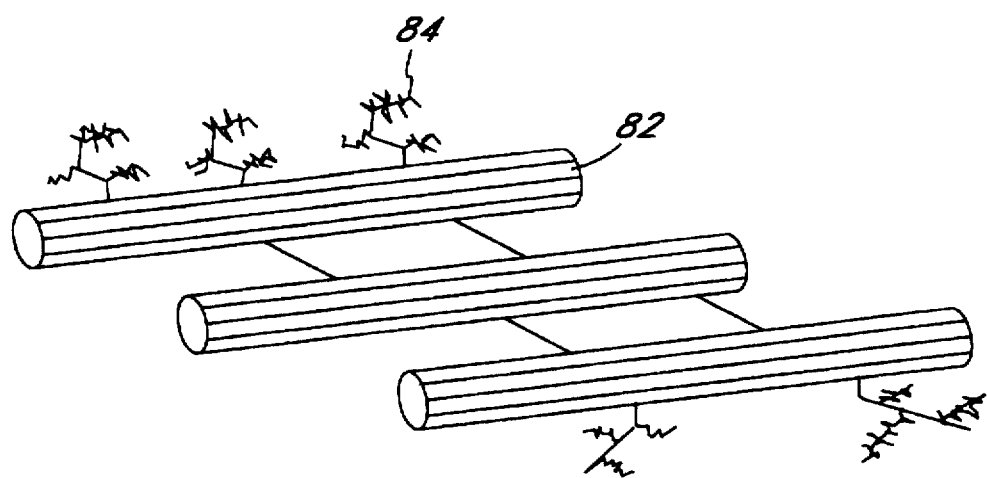

In accordance with the present invention, there has been provided an improved Orthokeratology method which the inventor refers to as Enzyme-Orthokeratology. Enzyme-Orthokeratology includes the use of one or more enzymes and/or the use of other agents in the Orthokeratology contact lens program. In the traditional Orthokeratology program, the cornea is merely bent or compressed, while the underlying structural components remain unchanged. In the methods of Enzyme-Orthokeratology, on the other hand, the cornea is softened, that is, the structural components of the cornea are partly degraded and/or modified, so that such structural components can be reformed. In this way, the cornea can take on and hold a new shape, preferably without any need for the continued use or support of contact lenses. Although some structural components of the cornea are located in the epithelium 70 (FIG. 10a), the Bowman's membrane 72, Descemet's membrane 74, and in the endothelium 76, the primary structural components of the cornea are located in the stroma 78. As shown schematically in FIG. 10B, the structural components of the stroma include collagen fibrils 82 and proteoglycans 84. In the methods of Enzyme-Orthokeratology, enzymes and/or other agents which degrade such structural components are administered to the cornea in order to soften it and make it more pliable. The term "soften" is used herein to denote the modification or degradation of one or more of the structural components of the cornea, which results in the cornea becoming softer and more pliable. The cornea can then be reshaped using a contact lens or other means.

I. Enzymes and Other Agents Used in Enzyme-Orthokeratology

A number of enzymes may be used to perform the corneal softening function of Enzyme-Orthokeratology. However, Enzyme-Orthokeratology is not limited to the use of enzymes. Also included are a number of other agents, including drugs and chemicals, which can be administered to soften a cornea in addition to or instead of administering enzymes. Of particular interest are agents which activate or inhibit enzymes. Agents other than enzymes can also be used to accomplish aspects of Enzyme-Orthokeratology besides corneal softening.

A. Exogenous Enzymes Used in Enzyme-Orthokeratology

Enzymes are protein molecules that speed up chemical reactions. In order to increase the rate of a reaction, an enzyme combines with one or more substrate molecules to form a complex molecular structure which catalyzes the chemical reaction of the substrate or substrates. The enzyme, which remains unchanged by the reaction, then separates from the product or products of the reaction.

In one aspect of the present invention, exogenous enzymes are administered to a subject in order to soften the cornea of that subject. Exogenous enzymes are those derived from outside the eye of the subject, such as an enzyme purified from an animal, vegetable, or microbial source. Such enzymes must be administered so as to pass such enzymes into the cornea of a subject.

In a preferred embodiment of the present invention, the primary enzyme used to soften a cornea is hyaluronidase. Hyaluronidase is an enzyme that degrades mucopolysaccharides. Specifically, it catalyzes the hydrolysis of the one to four linkages in hyaluronic acid, chondroitin, and chondroitin 4 sulfates A & C. Thus, it is able to break down mucopolysaccharide chains. Mucopolysaccharide is one of the intracellular ground substances (cement or glue) of the stroma, the connective-type tissue of the middle layer of the cornea.

The shape of the cornea is largely dependent on the arrangement of collagen fibrils in the stromal layer of the cornea and on the arrangement of the mucopolysaccharide layers between these fibrils. Hyaluronidase, which is specific to only the mucopolysaccharide layer, breaks down mucopolysaccharide chains when released into the cornea. The stroma is thereby temporarily softened and the cornea becomes more pliable.

Hyaluronidase may be obtained from any of a variety of sources, including bovine (bull) testes, ovine (sheep) testes, and Streptomyces (bacteria). The hyaluronidase enzyme is preferably used as a lyophilized powder (freeze dried). One form of hyaluronidase is available under the trade name Wydase®, available from Wyeth Laboratories, Inc., Philadelphia, Pa. The Wydase® hyaluronidase is a preparation of highly purified bovine testicular hyaluronidase, and is available in two dosage forms. The lyophilized form is available as a sterile, white odorless amorphous solid powder and may be reconstituted with sodium chloride injection USP before use, typically in the proportions of about 1 milliliter per 150 USP units of hyaluronidase. A hyaluronidase solution is also available, containing 150 USP units of hyaluronidase per ml, with 8.5 mg sodium chloride, 1 mg edetate disodium, 0.4 mg calcium chloride, monobasic sodium phosphate buffer, and no more than about 0.1 mg thimerosal.

In a preferred embodiment, the lyophilized form of the hyaluronidase enzyme is placed in a solution comprising sodium phosphate, a buffer to keep the pH proper; sodium chloride; distilled $H_2O$, to dissolve the enzyme; bovine or human albumin, to preserve the effectiveness and activity of the enzyme; and other agents such as HCl and sodium hydroxide to adjust the pH up or down. Other drugs such as proparacaine hydrochloride may be included to anesthetize the cornea.

The optimuin hyaluronidase enzyme concentration will vary depending upon the length of the overall protocol, the nature of the drug delivery vehicle, the number of administrations, and possibly the degree of change in shape desired in a given patient. In general, concentrations within the range of from about 50 units/10 μl to about 3,000 units/10 μl, preferably within the range of from about 500 units/10 μl to about 1,000 units/10 μl, and most preferably about 1,500±10% units/10 μl, are used.

A sample enzyme formula to produce a formulation having about 1,000 units/10 μl would be as follows: 100,000 units of bovine hyaluronidase enzyme (lyophilized powder form) is combined with 1 ml distilled $H_2O$ and sufficient NaCl, $NaPO_2$ dibasic, and bovine serum albumin to produce an isotonic solution. The pH is tested and maintained at a level of 5–7 (near the biological pH). HCl (0.05 molar) drops can be added to lower the pH and NaOH added to increase the pH in order to establish and maintain an appropriate pH.

It has been found that an appropriate dose of hyaluronidase for softening a cornea in a mammal is between approximately 50 units of enzyme per milligram of substrate to approximately 5,000 units per milligram of substrate, in this case the mucopolysaccharide of the cornea. Dosages between 100 and 1,500 units per milligram of substrate in particular have been found to be safe and effective. At lower dosages, multiple administrations may have to be made, where a single administration can be effective when a higher dose of enzyme is used.

Other enzymes which act on the proteoglycan structural components of the cornea can also be used to soften a cornea in accordance with the present invention. For example, enzymes such as chondroitinase ABC, chondroitinase AC, keratanase, and stromelysin can be used in place of or in addition to using hyaluronidase. These additional enzymes work on various proteoglycan components of the cornea, as shown in Table 1 below. In a preferred embodiment, a combination of enzymes is used to soften the cornea of a patient. By breaking down different structural components of the cornea at the same time, it is believed that the cornea can be softened more quickly. An example of a preparation for breaking down proteoglycans is Dispase™, available from Boehringer Mannheimm Biochemicals (Indianapolis, Ind.), which comprises a non-specific neutral protease from *Bacillius polymyxa*.

TABLE I

| ENZYMES Specific for PROTEOGLYCANS | |
|---|---|
| ENZYME | SUBSTRATE |
| Chondroitinase ABC | Chondroitin sulphate |
|  | Dermatan sulphate |
| Chondroitinase AC | Chondroitin sulphate |
| Endo B-galactosidase (Keratanase) | Keratan sulphate |
| Hyaluronidase | Hyaluronate, Chondroitin |
|  | Chondroitin sulphate |
| Stromelysin | Proteoglycans |
| (Matrix metalloproteinase 3) | (Specific sites unknown) |
| Hyaluronidase | B-N-acetyl hexosamine (1–4) |
| (Bovine Testes) | glycosidic bonds of hyaluronic acid, chondroitin and chondroitin sulphate |
| Hyaluronidase (Leeches) | Specifically cleaves B-glucuronate (1–3) GlcNAc glycosidic bonds in hyaluronic acid |

Enzymes which act to break down the collagen components of the cornea can also be used in the methods of the present invention to soften a cornea. As shown in Table 2 below, matrix metalloproteinase 1 and matrix metalloproteinase 2 break down various types of collagen. Such enzymes can be used individually or in combination with enzymes that break down proteoglycan components of the cornea. Of course, other corneal softening agents can also be used in conjunction with enzymes that act on proteoglycan or collagen components of a cornea. Other enzymes or formulations can also provide acceptable results, as can be readily determined through routine experimentation by one of skill in the art in view of the present disclosure.

TABLE II

| ENZYMES Specific for COLLAGENS | |
|---|---|
| ENZYME | SUBSTRATE |
| Interstitial Collagenase (Matrix Metalloproteinase 1) | Types I, II, III |
| Gelatinase (Matrix Metalloproteinase 2) | Types IV, VII and Denatured Types I, II, III |

B. Endogenous Enzymes Used in Enzyme-Orthokeratology

In another embodiment of the present invention, endogenous enzymes, enzymes that are already present in the eye of a subject, are used to soften a cornea rather than using exogenously derived enzymes. Endogenous enzymes capable of breaking down the structural components of the cornea generally exist in the eyes of mammals in an inactive state. In order to utilize such enzymes, therefore, the enzymes must first be activated.

The mechanism of activation of an endogenous enzyme will, of course, vary from enzyme to enzyme. Endogenous enzymes which are metalloproteinases, for example, can be activated by the administration of an activator such as interleukin-1 α. Other known activators of metalloproteinases which are believed to be effective include tumor necrosis factor, monosodium urate monohydrate, 4-amino phenylmercuric acetate, human serum amyloid A, human $B_2$ microglobin, and copper chloride. Similarly, it is believed that endogenous enzymes that break down proteoglycan components of a cornea can be activated with activators of those enzymes.

Alternatively, endogenous enzymes can be activated by inactivating inhibitors of those enzymes. For example, iodoacetamide, available from Sigma Chemical (St. Louis, Mo.), can be administered to a cornea in order to inactivate inhibitors of endogenous metalloproteinase enzymes. Once the inhibitor of the endogenous enzyme is itself inactivated, the endogenous enzyme becomes active.

C. Inhibitors of Enzymes Used in Enzyme-Orthokeratology

In a further aspect of the present invention, inhibitors of enzymes and agents which break down the structural components of a cornea are disclosed. Such inhibitors are used to slow or stop softening reactions in a cornea, thereby controlling the rate and/or amount of corneal softening produced by the administration of an enzyme or agent to the cornea. By slowing or stopping the softening of a cornea, it is believed that an inhibitor allows a subject's natural mechanisms fore repairing or replacing damaged or modified structural components of the cornea to begin the process of rebuilding the cornea and returning it to its previous structural integrity. This process can be referred to as the "hardening" of the cornea. Inhibitors can therefore be used to more closely control the amount of softening which occurs as the result of the administration of an enzyme or agent which produces corneal softening.

Included among the inhibitors of the present invention are inhibitors of specific enzymes used to soften a cornea. These inhibitors stop the softening process by inhibiting the enzymes which break down the collagen, proteoglycan, and other structural components of a cornea. Alternatively, inhibitors can act by sequestering an activator of an enzyme that breaks down corneal structural components, or can act by otherwise preventing an activator from activating such enzymes. If a non-enzymatic means of softening a cornea such as a chemical means is used, an inhibitor can be used that sequesters or deactivates such a softening means in the corneal environment.

The inhibitors of the present invention which act to inhibit enzymes can be inhibitors of either exogenous or endogenous enzymes. For example, if an exogenous metalloproteinase enzyme is administered to soften a cornea, a metalloproteinase inhibitor can be administered when it is desired to slow or halt the softening activity of the metalloproteinase enzyme. Included among such inhibitors are EDTA (ethylene diamine tetracetic acid), N-ethylamine, cycloheximide, 1,10 phenatroline, and phenylmethane sulfonyl fluoride. If it is desired to inhibit a collagenase enzyme, EDTA or cysteine can be administered. And if the enzyme is one that breaks down mucopolysaccharides such as hyaluronidase, ferric ($Fe^{2+}$) or cupric ($Cu^{2+}$) ions at a concentration of about $10^{-5}M$ can be administered. One of skill in the art can also identify known inhibitors of other endogenous and exogenous enzymes.

D. Determining Enzymes and Inhibitors and their Dosages

The enzymes, inhibitors, and other agents, used in the methods of the present invention, in addition to the proper dosages of such agents, can be determined by one of skill in the art through routine experimentation. Such experimentation can comprise testing a dose of an enzyme, inhibitor or other agent on donor globes (eyes) mounted in plastic model sockets or testing such a dose on laboratory animals. Briefly, to determine an appropriate corneal softening amount of a known softening agent or an agent to be tested for its ability to produce corneal softening, a dose of the enzyme or agent is administered to a cornea in a donated eye or a cornea of a test animal, and the softening effect of the agent is thereafter determined.

In order to determine whether an enzyme is effective in softening a cornea, or if the enzyme is a known softening agent, whether a particular dosage of the enzyme will product corneal softening, the enzyme is first mixed in a carrier vehicle that is pharmacologically acceptable to a mammal. Preferably, the enzyme used is in lyophilized (dry powder) form, and is dissolved in isotonic saline. However, one of skill in the art will understand that a variety of pharmacologically acceptable carriers which do not interfere with the functioning of an enzyme can be used.

A test dose of the enzyme in solution is then administered to a test cornea in order to determine its corneal softening effect. In one procedure for testing enzymes, the enzyme being tested is first administered to donor globes (eyes from a human donor) mounted in plastic sockets. This procedure is particularly preferred for determining the effect of an enzyme on a human cornea because in this way a human cornea can be tested without subjecting a living person to experimentation. A donor globe used in this procedure is prepared for experimentation by injecting it with sufficient saline to maintain the intraocular pressure of the globe at approximately 20 mm Hg.

The test dose of enzyme is then administered to the donor cornea. Such administration can be, for example, by injection of the enzyme into the cornea. Normally, the lens will become opacified following this step due to the introduction of water into the eye and a change in the refractive index of the eye. After a test period of time, the mounted globe is then examined to determine whether any corneal softening has occurred, and if so the extent of such softening.

The examination of the cornea can be performed, for example, through slit-lamp examination, which can determine the presence and clarity of a cornea. If no cornea is left after the treatment, then the dosage used in that case is an overdose. If the cornea has not disintegrated, then a number of determinations can be made to determine the extent of any corneal softening following treatment, as is known to one of skill in the art. For example, the treated cornea can be further subjected to (1) pachymetry, to measure the thickness of the cornea; (2) computer assisted corneal topography, to evaluate the surface topographical change; (3) a measurement of the tensile strength of the cornea; (4) a measurement of the distensibility of the cornea in response to increased intraocular pressure; (5) keratometry, to measure central corneal curvature; and (6) retinoscopy, to measure the refractive error of the cornea. The values determined through these tests can be compared to values determined prior to the administration of the enzyme.

In addition, a treated cornea in a mounted globe can be subjected to a number of other tests in order to determine the strength and viability of the cornea following treatment. For example, light, scanning, and transmission electron microscopy can be used to examine the morphology of the cornea; a tissue culture can be prepared to determine the viability of the cells of the cornea following treatment; biochemical studies can be made of the collagens and other structural components of the cornea following treatment, including the use of an optical multichannel analyzer which allows spectroscopy of the corneal tissue; and immunofluorescent studies with antibodies specific for structural components of the stroma and for the enzymes tested can be performed. The immunofluorescent test can be used in particular to evaluate the binding sites in the cornea of the enzyme tested.

The foregoing tests of donated globes and corneas can be used to verify that the use of a particular enzyme does not compromise the transparency of the cornea, decrease the viability of the corneal cells, or damage the structural integrity of the cornea. Testing the use of an enzyme on the cornea of a test animal, however, is also desirable in order to make sure that the enzyme has no unexpected effect in living mammals that is not discovered during tests of donated globes. In order to test the effect of a particular test enzyme, a test dose of the enzyme in a pharmacologically acceptable carrier solution is administered to a test animal, in this case a mammal, so as to deliver that enzyme to the cornea of the animal.

Following the administration of enzyme to the cornea of the animal, the animal's cornea can be subjected to the following examinations: pachymetry, to measure corneal thickness; computer assisted corneal topography to evaluate the surface topographical change of the cornea; slit lap examination to determine the clarity of the cornea, anterior chamber and iris; tonometry, to measure intraocular pressure; fundoscopic examination, in order to evaluate the optic nerve and retina; keratotomy, to measure central corneal curvature; retinoscopy, to measure refractive error; and staining with fluorecein or Rose Bengal to identify damage to the corneal epithelium. The values determined through these tests can be compared to values determined prior to the administration of the enzyme, as well as to values determined with respect to the untreated eye of the animal.

Activators of endogenous enzymes and other corneal softening agents not disclosed herein and proper doses of such known and unknown agents can be determined as described above in relation to determining enzymes and doses of enzymes.

In order to determine whether an agent acts as an inhibitor of corneal softening, or to determine whether a particular dosage of an inhibitor is effective, a corneal softening amount of an exogenous enzyme, an activator of an endogenous enzyme or other corneal softening agent is first administered to a plurality of donor globes or to the corneas of an experimental animal, as described above. When using experimental animals, once the corneas have begun to soften, one cornea of the experimental animal is then treated with a test dose of the inhibitor or the agent to be tested for its inhibitory effect in order to determine whether the does of the inhibitor or test agent can stop the softening process. The other cornea is left alone as a control. When using donor globes, a plurality of corneas can be tested, as long as one is left untreated as a control. The treated corneas can then be tested with a does of inhibitor or test agent. The control cornea and tested corneas should be treated for approximately the same amount of time in order to be able to make a valid comparison of the effectiveness of the inhibitors and test agents on the tested cornea.

After a test period of time, the softness or extent of degradation of the structural components of each of the corneas are compared using the procedures described above with reference to determining the extent of corneal softness when testing enzymes as softening agents. If the inhibitor-treated cornea is less soft than the untreated cornea, this indicates that the test dose of the inhibitor is useful in inhibiting the softening process.

II. Methods of Administering Enzymes/Agents

The foregoing enzymes and agents for softening a cornea can be administered in any way known to the art. For example, an enzyme or agent can be injected directly into the eye in a location proximal to the cornea. In this embodiment, the enzyme or agent should be mixed in a pharmacologically acceptable carrier which is acceptable to the subject and which will not alter the effectiveness of the enzyme or agent. The use of injection as the method of administration is particularly preferred when the agent or enzyme is a large molecule. The term "large molecule" denotes a molecule which is too large or has too high a molecular weight to diffuse into the cornea from the outside surface of the eye or diffuses too slowly to have any appreciable softening effect, and so must be delivered by some means other than unaided diffusion. This term also denotes any molecule which cannot so diffuse into the cornea for any other reason.

Injection, however, is a method of administration that is unpleasant to a subject and is therefore not preferred when other means of delivering an enzyme or agent are possible. Means of aiding diffusion across the eye into the cornea are more preferred. Such means include, for example, the use of liposomes to deliver the enzyme or agent. The enzyme or agent is packaged into liposomes, which can pass across the lipid soluble membrane of the corneal epithelium and into the corneal stroma. Other means of aiding diffusion include the use of an electrical current to make the outer membrane of the eye more permeable to the passage of enzymes and agents, known as iontophoresis.

In a more preferred embodiment, the enzymes and agents used to soften the cornea of a subject are administered in the form of an eye drop. This method of administration is particularly preferred when the agent or enzyme being delivered is not a large molecule. For example, iodoacetamide can be administered in the form of an eye drop. A solution of 0.05% to 0.25% (g/100 ml volume) iodoacetamide is prepared by dissolving 0.05 g to 0.25 g iodoacetamide in 100 ml isotonic saline. One to two drops of the solution is then administered every hour for about four hours to a subject.

An even more preferred method of administering agents and enzymes involves the administration of agents and enzymes directly from a contact lens. As will be discussed in more detail below, the methods of the present invention involve the application of a rigid contact lens to a softened cornea in order to reshape that cornea to a desired configuration. In this embodiment of the present invention, the fitting of the contact lens and the administration of an enzyme and/or agent occurs simultaneously. This embodiment is most preferred when the enzyme and/or agent is not a large molecule and is thus able to diffuse from the outer surface of the eye into the cornea.

As an example of this embodiment of the present invention, a corneal softening amount of the hyaluronidase enzyme formula described above is loaded into a chamber inside a rigid contact lens, preferably one which is gas permeable. Such a lens can comprise one of the lenses shown in FIGS. 2, 4D, 5D, 12, and 14 which has a chamber for storing a solution of the enzyme or agent. Alternatively, the enzyme or agent can be loaded or impregnated into a soft lens capable of taking up the enzyme or agent by soaking the soft lens in a solution containing the enzyme or agent. The enzyme or agent can also be loaded into a combination of a soft and a rigid lens, as shown in FIG. 8B.

In all of the foregoing embodiments of a contact lens for administering enzyme or agent, the enzyme or agent is administered as it diffuses out of (is released from) the chamber in the lens or the material of the lens (if the enzyme or agent is soaked into a soft lens). If the enzyme used is hyaluronidase, dosage volumes are typically in the range of from about two drops to about six drops, and preferably between about three drops and five drops of the 500 units/µl formulation described above. Dosages for different refractive conditions and contact lens delivery vehicles can be optimized through routine experimentation by one of skill in the art.

Figure 1:
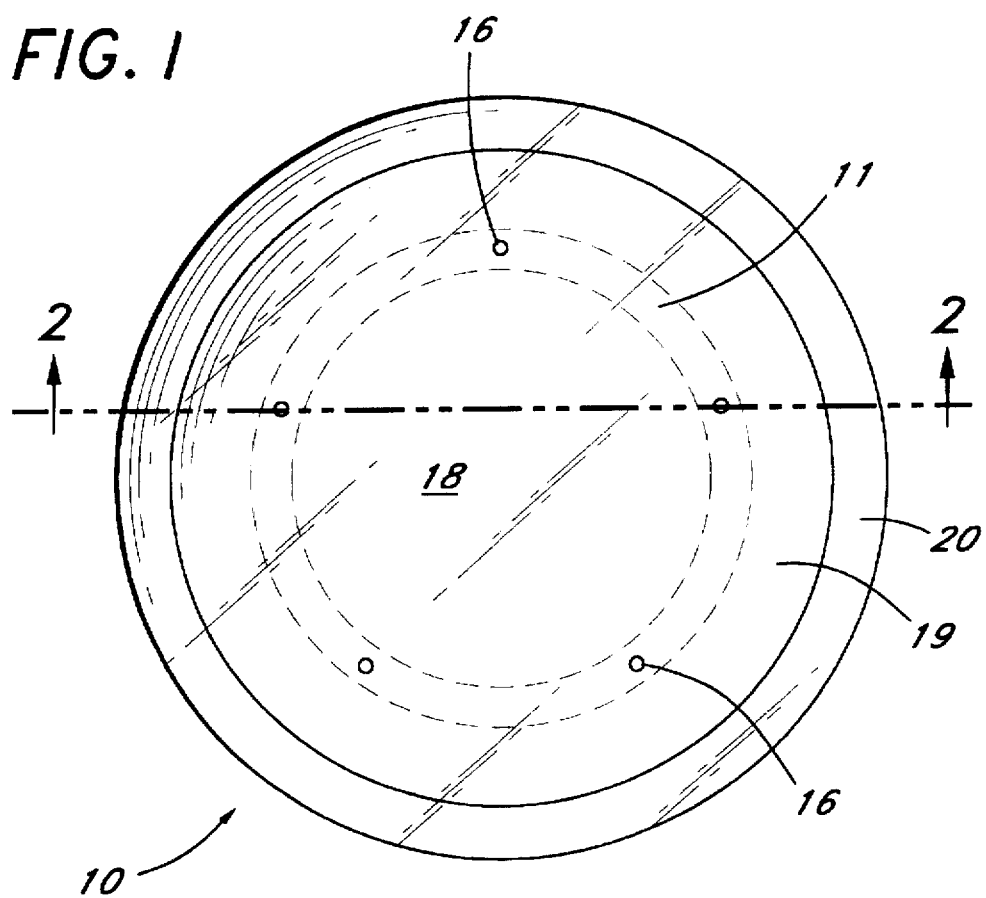
FIG. 1 is a plan view of an Enzyme-Orthokeratology rigid gas permeable contact lens for myopia.
Figure 2:
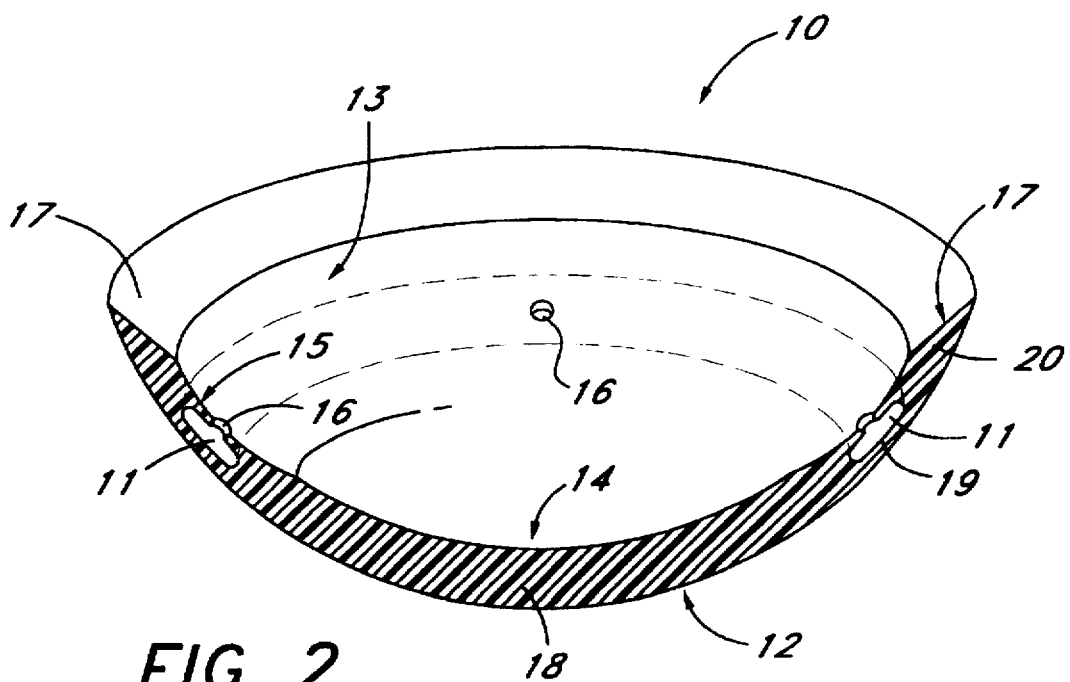
FIG. 2 is a cross-sectional view taken along the lines 2—2 on FIG. 1.

In accordance with one method of administration through contact lenses of the present invention, enzymes and agents can be applied to the eye through the use of rigid contact lenses 10 as shown in FIGS. 1–2. These lenses can be made from known fluoro silicone acrylate lens materials which are gas permeable. The lens is provided with an internal chamber 11 for storing the cornea softening agent. Thee chamber 11 preferably comprises a radially symmetrical space encircling the entire lens 10 between the anterior surface 12 and posterior surface 13 of the lens 10.

Rigid lenses for the present purpose can conveniently be made by lathe cutting, molding, or milling a posterior component and an anterior component from a contact lens button which, during fabrication, can be secured together to form a unitary lens using bonding techniques or adhesives known in the art. The chamber 11 can be formed by lathe cutting an annular recess into the convex surface of the posterior component of the lens before the final lens fabrication. Although any of a variety of dimensions can be used in accordance with the present invention, a preferred lens 10 is provided with an annular chamber 11 having a width of approximately 1.0 mm to about 1.5 mm and a depth of from about 0.05 mm to about 0.10 mm.

A plurality of microscopic holes 16 are provided in the posterior portion of the lens 10 to allow fluid communication between the chamber 11 and the eye, thereby facilitating the timed release of the enzyme/agents into the cornea. These holes 16 may be provided by mechanical or laser drilling, or by molding prior to assembling the anterior component and posterior component of the lens. Preferably, holes 16 are drilled using a mechanical drill having a microcarbon drill bit.

The pumping action of the eyelids combined with natural tearing assists the release of the enzyme or agent through the tiny holes 16. Preferably, the holes are produced by mechanical drilling with a microcarbon bit and will have a diameter of from about 0.002 mm to about 0.010 mm, and preferably about 0.005 mm. The number and diameter of the holes 16 can be varied to affect the time release characteristics, as will be apparent to one of skill in the art. In general, however, for the diameter ranges specified above, from about 3 to about 10 holes are contemplated to be used.

In a preferred embodiment of the lens 10 of FIGS. 1 and 2, the posterior portion of the lens has a centerpoint thickness of approximately 0.12 mm and an annular recess is lathed to a depth of about 0.075 mm. A number of holes 16, each having a diameter of about 0.005 mm, are drilled through the bottom of chamber 11 and spaced equidistantly apart around the periphery of the chamber 11 to provide communication with the posterior surface 13 of the lens. Although five holes are shown in FIG. 1, the number of holes will vary, depending on the desired rate of administration of enzyme or agent from the chamber 11.

The anterior portion of the lens, having a centerpoint thickness of about 0.12 mm is thereafter secured to the posterior portion to enclose the annular recess and form chamber 11, thereby forming a lens having an overall center thickness of about 0.24 mm. Bonding can be accomplished by applying a small amount of a bonding agent such as Concise™ enamel bonding system sold by 3M (St. Paul, Minn.). Other means of joining the posterior and anterior portions of the contact lens will be apparent to those of skill in the art.

Posterior radii of curvature (Base curve 14, intermediate curve 15 and peripheral curve 17) of the lens 10 are selected that will reshape the anterior corneal curvature to a shape required for rendering the eye emmetropic (no correction). The posterior and anterior configurations of the contact lens in accordance with the present invention are similar to those used in conventional Orthokeratology fitting procedures. In general, the convex anterior surface of the lens 12 approximates a substantially uniform radius of curvature along all planes, and can vary from an aspherical design, a tenticular design, a spherical design, or any other configuration necessary to accommodate the fitting needs of a patient. The concave posterior surface 13 of the lens 10 is divided into several discrete zones, each having a unique curvature. For example, referring to FIG. 2, a posterior central base curve 14 is radially symmetrically disposed about the centerpoint of the lens 10. An intermediate posterior curvature 15 is disposed annularly about the radial outer periphery of the posterior central base curve 14. Adjacent to the radially outward side of the intermediate posterior curvature 15 is a third peripheral posterior curvature 17. Thus, the lens 10 can be considered to comprise three distinct zones shown in FIG. 1, a central optic zone 18, an intermediate zone 19, and a peripheral zone 20. Preferably, in accordance with the present invention, an annular chamber 11 is disposed within the intermediate zone 19.

Figure 12:
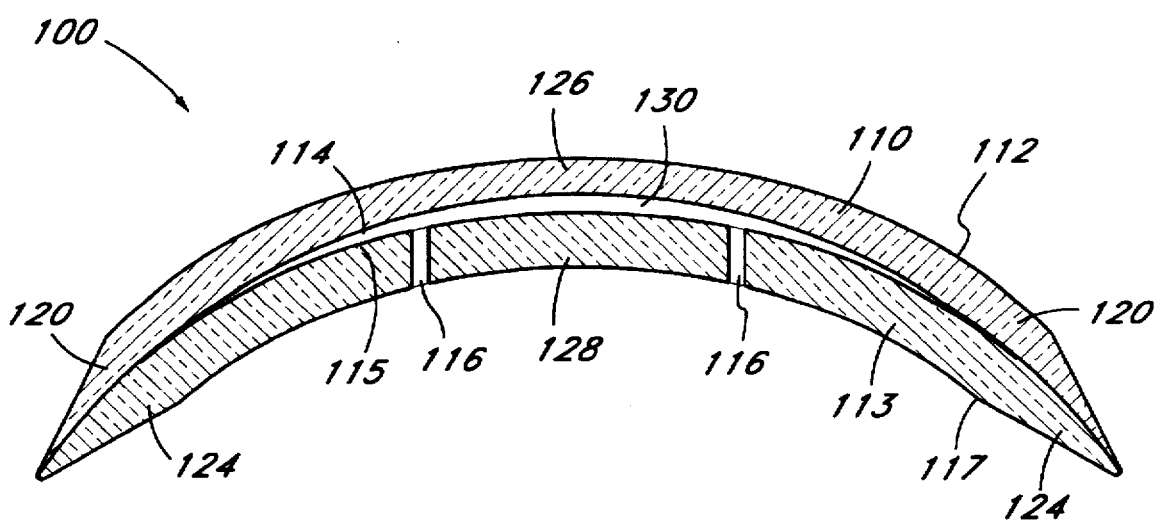
FIG. 12 is a cross-sectional view of the contact lens of FIG. 11 along line 12—12.
Figure 14:
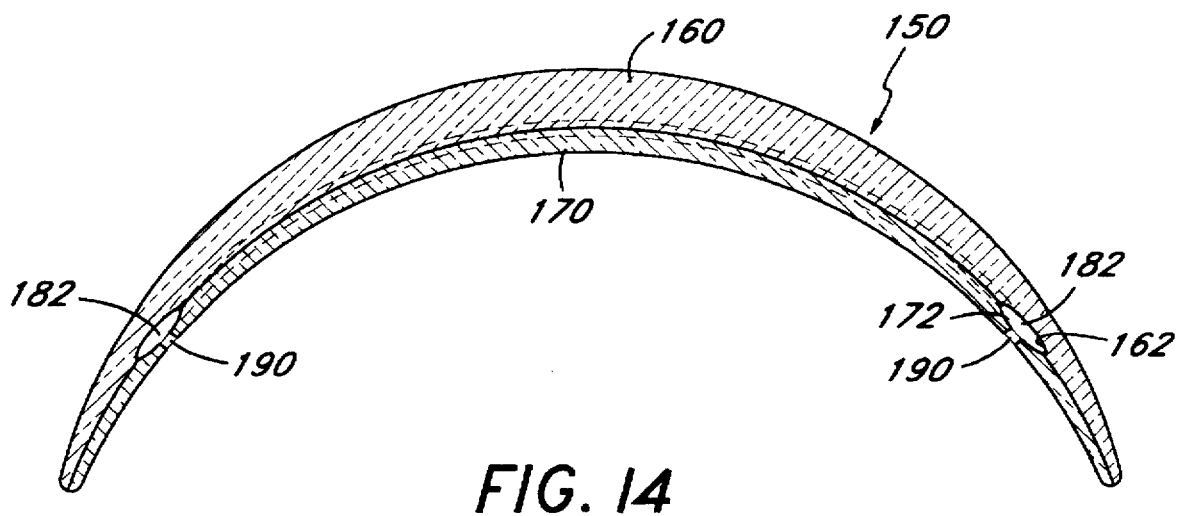
FIG. 14 is a cross-sectional view of the contact lens of FIG. 13 along line 14—14.

In another aspect of the present invention, a contact lens is provided which is composed of two layers which are laminated together, as shown in FIGS. 12 and 14. In this improved design for a contact lens of the present invention, larger chambers for storing enzyme or agent can be created.

In this contact lens, an anterior portion 110 of the contact lens 100 is manufactured having an anterior surface 112 and a posterior surface 114. A posterior portion 113 of the contact lens 100 is also manufactured with an anterior surface 115 and a posterior surface 117. The outer perimeter 120 of the posterior surface 114 of the anterior portion 110 is designed to have the same radius of curvature as the outer perimeter 124 (best shown in FIG. 11) of the anterior surface 115 of the posterior portion 113. In this way, when the posterior surface 114 of the anterior portion 110 and the anterior surface 115 of the posterior portion 113 are laminated together, a seal is formed between the outer perimeters 120, 124 of the anterior and posterior portions.

However, in a central portion 126 of the anterior portion 110, the posterior surface 114 has a steeper radius of curvature than the anterior surface 115 of a central portion 128 of the posterior portion 113. Because of this steeper radius of curvature, when the anterior portion 110 and the posterior portion 113 are laminated together, a chamber 130 is formed between the central portion 126 of the anterior portion 110 and central portion 128 of the posterior portion 113 of the contact lens 100. The volume of the chamber 130 can be adjusted by changing the radii of curvature of the posterior surface 114 of the central portion 126 and of the anterior surface 113 of the central portion 128, as will be apparent to one of skill in the art.

Prior to manufacture, one or more holes 116 are made in the central portion 128 of the posterior portion 113 of the contact lens of this design. Preferably, the holes 116 are produced by mechanical drilling with a microcarbon bit or by means of a laser such as an argon laser, and will have a diameter of from about 0.002 mm to about 0.010 mm, and preferably about 0.005 mm. The number and diameter of the holes 16 can be varied to affect the time release characteristics, as will be apparent to one of skill in the art. Thus, the rate at which a dose of an enzyme or agent is dispensed from the chamber 130 is largely controlled by the size and number of holes present in the central portion 128 of the posterior portion 113 of the lens 100. In general, however, for the diameter ranges specified above, from about 3 to about 10 holes are contemplated to be used. Preferably, these holes 116 are spaced around the central portion 128 of the posterior portion 113 of the contact lens 100 in order to provide communication between the chamber 130 and the surface of the eye of a subject wearing the lens 100.

In a preferred embodiment of the lens 100 of FIG. 12, the posterior portion 113 of the lens 100 has a centerpoint thickness of approximately 0.125 mm. The anterior portion 110 of the lens 100 preferably has a centerpoint thickness of about 0.125 mm. When the anterior portion 110 and the posterior portion 113 are joined, a lens is created having an overall center thickness of about 0.24 mm. If it is desired to change the shape of a cornea with increased rapidity, a lens of increased thickness can be used which exerts more pressure on the cornea to conform to the desired configuration. Bonding can be accomplished by applying a sufficient amount of a bonding agent such as the Concise™ enamel bonding system sold by 3M (St. Paul, Minn.). Other methods of bonding will also be apparent to one of skill in the art.

As with other embodiments of the present invention, concave radii of curvature of the posterior surface 117 of the posterior portion 113 of the lens 100 are selected that will reshape the anterior corneal curvature to a desired shape required for modifying corneal curvature and reducing refractive error. Thus, the posterior and anterior configurations of the contact lens of this aspect of the present invention are similar to those used in conventional Orthokeratology fitting procedures, as previously described and as are known to those skilled in the art.

A lens of this embodiment of the present invention is preferably made from known fluoro silicone acrylate lens materials. Such rigid lenses can be made by lathe cutting, molding, or milling a posterior component and an anterior component from a contact lens button. After the anterior and posterior components are manufactured, they can be secured together to form a unitary lens using bonding techniques, adhesives, or any other method of attachment known to the art. For example, an enamel bond system can be used to join the anterior and posterior contact lens portions. An example of such a system is the Concise™ enamel bond system sold by 3M (St. Paul, Minn.).

Figure 11:
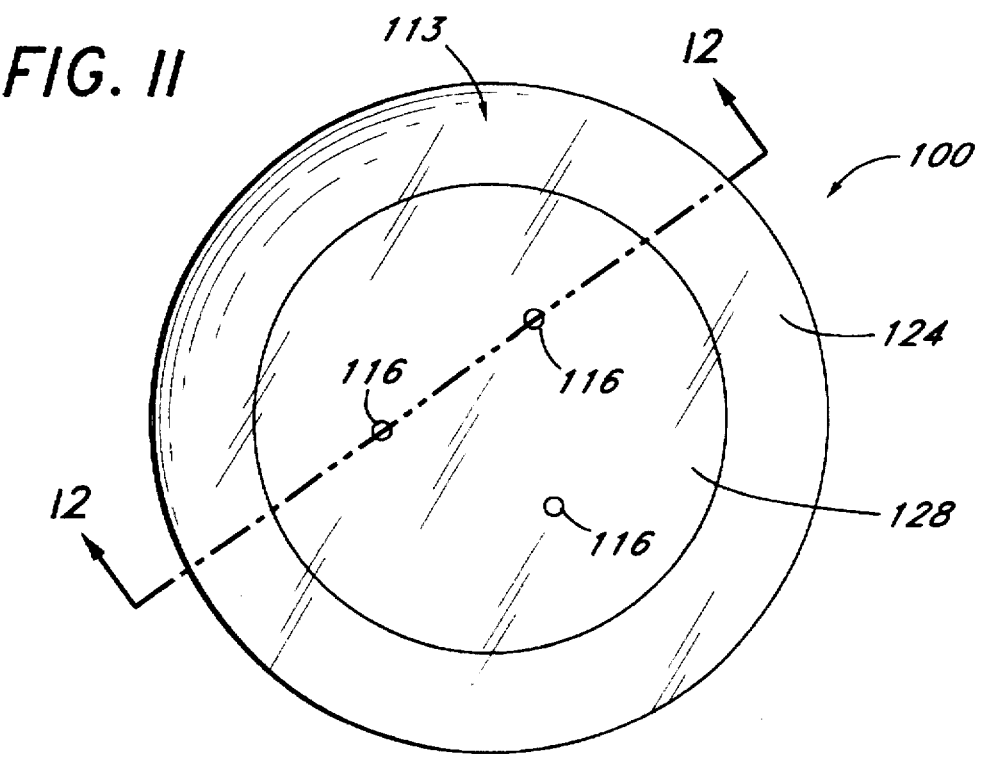
FIG. 11 is a plan view of the underside of a particular embodiment of a contact lens of the present invention.
Figure 13:
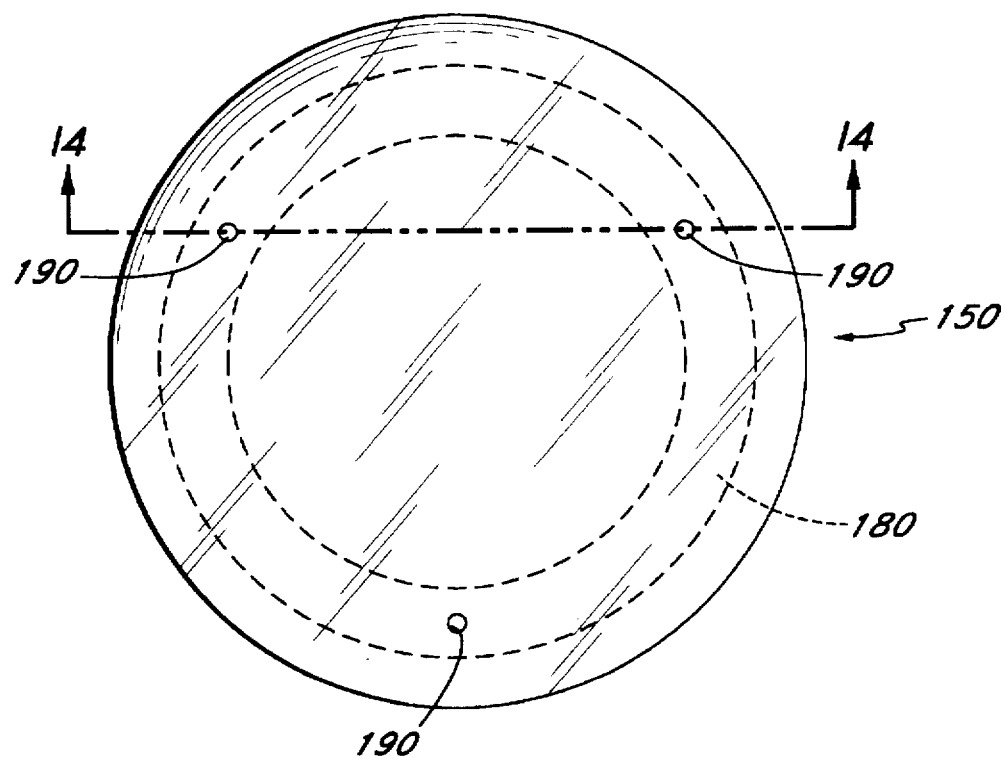
FIG. 13 is a plan view of the underside of another embodiment of a contact lens of the present invention.

In an alternate embodiment of a contact lens of this aspect of the present invention, a lens is provided which has a peripheral chamber rather than a chamber in the central portion of the lens as in the embodiment shown in FIGS. 11 and 12. This embodiment of the lens is shown in FIGS. 13 and 14. In the specific embodiment shown, the lens 150 is composed of an anterior portion 160 and a posterior portion 170 which are laminated together in the same way as the lens shown in FIGS. 11 and 12. In this embodiment, chamber 182 is provided in an intermediate portion 180 of the lens 150.

In the embodiment shown in FIG. 14, the chamber 182 is formed in the intermediate portion 180 of the lens 150 by providing an area of the posterior surface 162 of the anterior portion 160 of the lens 150, which has a steeper radius of curvature than that found in the remainder of the posterior surface of the anterior portion 160 of the lens 150. As in the foregoing embodiment of a chambered contact lens, the volume of enzyme or agent which can be contained in the lens and thus administered to a subject is largely determined by the radius of curvature of the posterior surface 162 of the anterior portion 160 of the lens 150 in the intermediate portion 180 of the lens, as well as by the radius of curvature of the anterior surface 172 of the posterior portion 170 of the lens 150 in the intermediate portion 180 of the lens.

The posterior portion 170 of the lens 150 is also provided with holes 190 through the posterior portion 170 of the lens 150 in the intermediate portion 180 of the lens. These holes serve to allow the transfer of the contents of the chamber 182 from the chamber 182 to the eye of the subject. The number and size of the holes 190 will largely determine the rate at which an enzyme or agent is delivered to the eye.

Although the embodiments of a chambered contact lens shown in FIGS. 11–14 have been described as being produced by laminating together an anterior portion and a posterior portion of the lens, one of skill in the art will recognize that other methods of forming the previously described chambers are also possible.

Day and/or night wear of these Enzyme-Orthokeratology lenses may be used. The cornea can generally be softened and reshaped in a matter of hours to a few days, and the reshaping progress can be monitored using conventional methods.

Figure 3A:
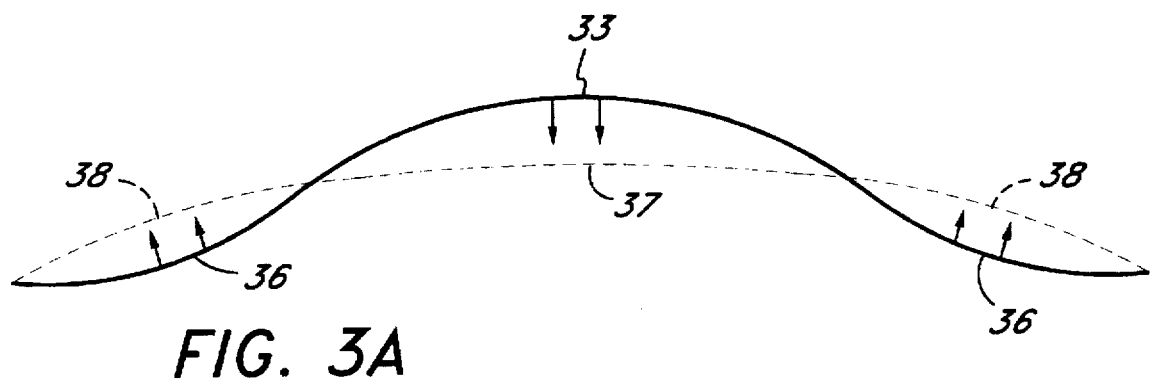
FIG. 3A is a schematic representation of the cross-sectional configuration of a myopic cornea, in solid lines, compared to the ideal shape shown in phantom, following the method of the present invention.

The lens 10 of the present invention can be utilized to correct myopia (FIG. 3A), astigmatism (FIGS. 4A–D), and hyperopia (as detailed infra). Hyperopia can be corrected (FIGS. 5A–B) with the lens designs shown in FIGS. 5C–D and FIGS. 15 and 16.

In accordance with a further delivery method of the present invention, a soft lens bandage or shield 22 (FIG. 6) is soaked or charged with a dose of the enzyme/agents. The soft lens is then properly fit to the cornea and worn for a matter of hours to release an enzyme and/or agent into the cornea. After the enzyme and/or agent sufficiently soften the corneal stroma, the soft lens either dissolves or is taken off.

One type of soft lens for use with this method is a collagen material which tends to uptake a relatively high volume of solution containing enzyme and/or agent and release them relatively slowly. The material may be highly purified bovine collagen. The diameter preferably ranges from about 13.5 mm to about 16 mm. Base curves preferably range from about 8.0 mm to about 9.5 mm. The DK (which is a measure of the oxygen permeability of a material) should be about 50 and the $H_2O$ hydration percentage should be about 83%. Of course, the enzyme or agent used in this embodiment should not normally be one which degrades collagen, such as collagenase.

One lens which has been found to be particularly well suited for the practice of this aspect of the present invention is the Medilens™ corneal shield available from Chiron Opthalmics, Inc. of Irvine, Calif. The Medilens™ corneal shield is a clear, pliable thin film fabricated from bovine tissue. This tissue has a high percentage of collagen closely resembling the collagen molecules of the human eye.

The Medilens™ corneal shield is stated to provide protection and lubrication to the ocular surface, gradually dissolving within approximately 24 hours. The dry weight of the lens is approximately 5.5 mg, and wet weight following loading with the enzyme of the present invention is approximately 34 mg. Loading is accomplished by soaking the lens in a solution, as previously described, for approximately 60 minutes at room temperature. The uptake of the lens has been measured to be approximately 28.5 mg, and the hydration of the lens is approximately 84%. In volume terms, the uptake of the lens is approximately 200–300 µl (microliter). This is equivalent to approximately 4–6 drops of solution or 28 mg at a 150 unit/ml concentration.

Other types of soft lens materials tend to uptake less of a solution containing an enzyme or agent and also to release it more quickly. Examples of such materials are common hydrophilic soft lens materials such as etafilcon A and phemfilcon A, available from Vistacon and Wesley Jessen. These lenses can be the disposable or long-term wear variety. Lens having an $H_2O$ content of between about 58% and about 70% have been found to be useful in the present method.

After the soft lens 22 or other delivery vehicle has released the enzyme and/or agent into the cornea and softened it, a rigid contact lens with no enzyme is then fit to the cornea. The rigid contact lens rapidly reshapes the softened cornea. A contact lens is used which has a posterior radius that will reshape the anterior cornea to a curvature required for emmetropia. The reshaping process may take from a few hours up to a few days.

In a preferred embodiment, the rigid contact lens is fitted over the central portion of a soft contact lens which has been loaded with an enzyme or agent while that soft contact lens is on the eye of a patient. Due to the intraocular pressure of the eye, the softened cornea will tend to steepen in curvature. While this may be desirable in the case of hyperopia, this should be controlled in treating myopia and other conditions. And even when treating hyperopia, the amount of deepening in corneal curvature should be controlled. Therefore, it is desirable to place a rigid contact lens over a soft lens which is delivering enzyme and/or agent in order to control the change in shape of the cornea prior to the time that a rigid lens is fitted directly onto the eye in order to reshape the cornea.

In a more preferred embodiment, a rigid lens is fused to the central portion of a soft contact lens which delivers enzyme or agent to the cornea. In this way, the chances of having errors due to an improper fitting of the rigid lens over the soft lens can be avoided.

In accordance with a further embodiment of the present invention, a saturn-type contact lens 24, such as the Soft-perm™ lens sold by Sola Barnes Hynds-Pilkington (FIG. 7), is utilized. This type of lens comprises a lens with a rigid center 26 and a soft lens peripheral skirt 28. The rigid, preferably gas permeable center 26 contains no enzyme and/or agent whereas the soft lens peripheral skirt 28 is soaked in a solution containing the enzyme and/or agent.

The peripheral skirt 28 of the saturn-type lens 24 may be manufactured from synergicon A copolymer available from Precision-Cosmet. The rigid non-hydrophilic center 26 is typically from about 5.5 mm to 6.5 mm in diameter and has only about 0.2% $H_2O$ absorption (FIG. 7). The outer periphery 28 is polymerized into a soft hydrophilic skirt extending circumferentially about the outer periphery of the center 26 and has a width of from about 3.0 to 4.0 mm, and about 25% $H_2O$ absorption. The base curve of this saturn lens is from 7.2 mm to 8.2 mm.

As the saturn-type lens 24 is worn, the enzyme/agents are released into the cornea from the soft peripheral skirt 28, softening the cornea in hours. The rigid center of the saturn lens 26 immediately begins reshaping the softened cornea. The rigid center 26 has a posterior radius of curvature that will reshape the anterior cornea to a curvature required for emmetropia as has been discussed. The cornea is reshaped from hours to a few days. The soft lens skirt 28 gives added comfort and less edge sensation which helps the Orthokeratology process and encourages retainer lens wear.

The enzyme and/or agent dissipates out of the cornea in a few days and the cornea then hardens to its new shape. The saturn lens 24 or another rigid retainer is preferably worn for a few more days to stabilize the new corneal shape. The lens is then removed.

A "fused soft lens" contact lens system 34 (FIGS. 8A and 8B) can also be used to release the enzyme and/or agent into the cornea and simultaneously reshape it. In this embodiment of the present invention, an annular ring 30 of soft lens type material is fused to the inside intermediate curve and peripheral curve of a rigid gas permeable contact lens 32. The resulting fused (soft) lens 34 is soaked in the enzyme/ agents, and the enzyme is retained in the soft lens portion 30. The enzyme is then time released into the cornea, which softens it.

The rigid preferably gas permeable center 32 has a posterior central curvature 35 that reshapes the anterior cornea's curvature to a shape which corrects refractive error, preferably a shape which renders the eye emmetropic. The rigid contact lens center 35 is preferably a fluoro-silicone-acrylate material with a Dk of about 60–92. The diameters vary from about 7.5 mm to 10.5 mm and the base curves 35 of the rigid lens 32 vary from about 7.0 mm to 9.0 mm. The "fused on" soft lens portion 30 is a hydrophilic soft lens material such as etafilcon A or phemfilcon A. Attachment of the annular ring 30 to the rigid contact lens 32 is accomplished by an adhesion process. The width of soft annular ring 30 varies between about 0.75 and 1.5 mm each side.

III. The Enzyme-Orthokeratology Procedure

The Enzyme-Orthokeratology contact lens must be properly fit to the anterior surface of the cornea. When a chambered contact lens is worn, the enzyme and/or agent is then time released and secreted through the corneal epithelium and Bowman's membrane, finally reaching the stroma (substantia propria).

Figure 3B:
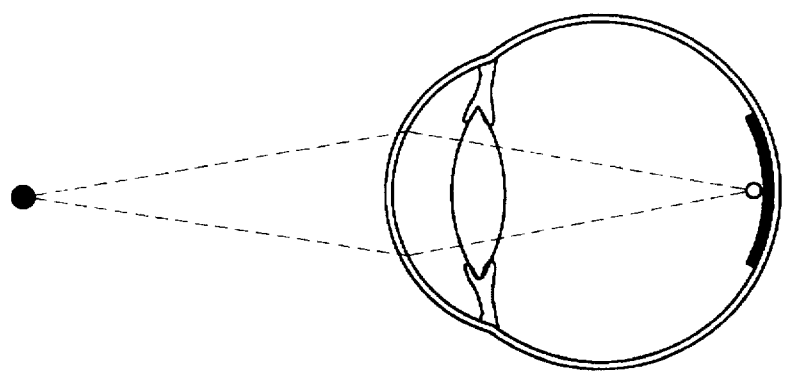
FIG. 3B is a schematic illustration of the convergence of light on the retina in an eye having normal vision.
Figure 3C:
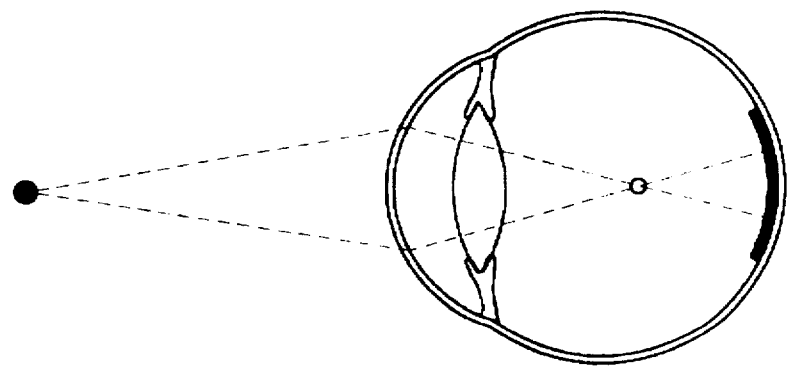
FIG. 3C is a schematic representation of the convergence of light in front of the retina in a nearsighted (myopic) eye.

In the case of myopia (FIG. 3A), the cornea usually begins with a positive shape, steeper in the center 33 and flatter in the periphery 36. After the rigid gas permeable lens is placed on the eye, and the force of the eyelids and lens movement cause flattening of the central corneal curvature 37. The internal pressure of the eye causes the paracentral cornea 38 to move outward or steepen. The cornea becomes spherical with a more minus shape and less central curvature (37, 38). The light entering the cornea is therefore refracted less, that is, further back towards the retina (FIG. 3B). This then reduces or eliminates myopia, which causes light to be refracted more and thus causes images to be focused in front of the cornea (FIG. 3C).

Once the proper corneal shape is achieved, the enzyme and/or agent dissipates out of the cornea and the cornea hardens. Alternatively, an inhibitor can be administered at this point to speed the hardening process. A retainer contact lens (not illustrated) is then worn for a short period of time (usually a few days) to stabilize the cornea, after which it is removed. The retainer lens can have the same rigid contact lens parameters as mentioned in relation to FIGS. 1 and 2. The retainer lens has no enzyme and is the final lens of the enzyme Orthokeratology treatment. Its posterior curvature helps the treated cornea retain the new corneal shape. The alignment of the repaired or replaced mucopolysaccharide chains and collagen fibrils conforms to the new shape imposed by the rigid lens. The structural components of the cornea retain this shape with a new memory of only the new shape. Stability and permanency is maintained without a retainer lens.

Contact lenses or spectacles will not be required for good visual acuity after the Enzyme-Orthokeratology lenses are removed. With previous Orthokeratology methods using no enzymes, if the retainer contact lenses were removed, the cornea would tend to regress back to its old shape, like a rubberband. This is because the unchanged mucopolysaccharides and collagen fibrils had a "memory" of the shape of the cornea before orthokeratology treatment.

The metabolic processes of the cornea are greatly accelerated at higher temperatures. Reshaping will occur more quickly if the corneal metabolism is increased by applying heat. Heat radiation and other methods of heating the cornea could possibly be used along with Enzyme-Orthokeratology if desired. Heat is generally not necessary to reshape the cornea, however.

A. Rigid Contact Lens Designs

One preferred embodiment of the rigid contact lenses designed for Enzyme-Orthokeratology comprises a lens made of a fluoro-silicone-acrylate material (methylmethacrylate difluoroitaconate siloxanyl copolymer) available from Paragon Optical. The high oxygen permeability of this material DK60-DK92×10−11, allows sleeping in the lens if necessary. The lens has excellent wettability with a low wetting angle of 26. The base curve of the lens varies from 6.5 mm to 9.0 mm, depending upon the central corneal curvature. The total diameter of the lens is the base curve in mm+1.3 mm to 1.8 mm, and the range is 7.5 mm to 10.5 mm (total diameter FIG. 1).

The central optic zone 18 (FIG. 1) is transparent and corrects the refractive error of the eye to produce excellent visual acuity. The optic zone diameter ranges from 6.5 mm to 9.0 mm. The intermediate zone 19 contains the chamber for enzyme and/or agent 11 to release the solution into the cornea. The width of the intermediate zone 19 varies from 0.35 mm to 1.0 mm. The intermediate curve 15 may be steeper or flatter than the base curve 14 of the lens depending on the refractive error. The peripheral curve 17 is flatter than the base curve 14 of the lens. The width of the peripheral zone 20 varies from 0.35 mm to 1.0 mm. The peripheral curves 17 allow for tear circulation and oxygen exchange during blinking.

The power of the lens is based on the refractive error of the patient and the lens base curve to central corneal curvature relationship. The thickness is 0.20 mm for 0 power; 0.01 mm should be subtracted for each diopter of minus correction, and 0.02 mm should be added for each diopter of plus. The inner curvature of the optic zone (14 FIG. 2) (base curve) is preferably calculated to make the eye emmetropic when the cornea is molded to this curvature. This may be accomplished with one to three lenses. The front curvature of the optic zone (12 FIG. 2) is of a radius calculated to give the subject no refractive error and 20/20 aided visual acuity while wearing the lens. The final lens will have zero refractive power. All of the rigid contact lens parameters vary depending upon the refractive error, corneal curvature and size, and fitting formula, as is known in the art. This lens design without enzyme may also be used to reshape the cornea after it has been softened with other enzyme releasing methods already mentioned.

Figure 15:
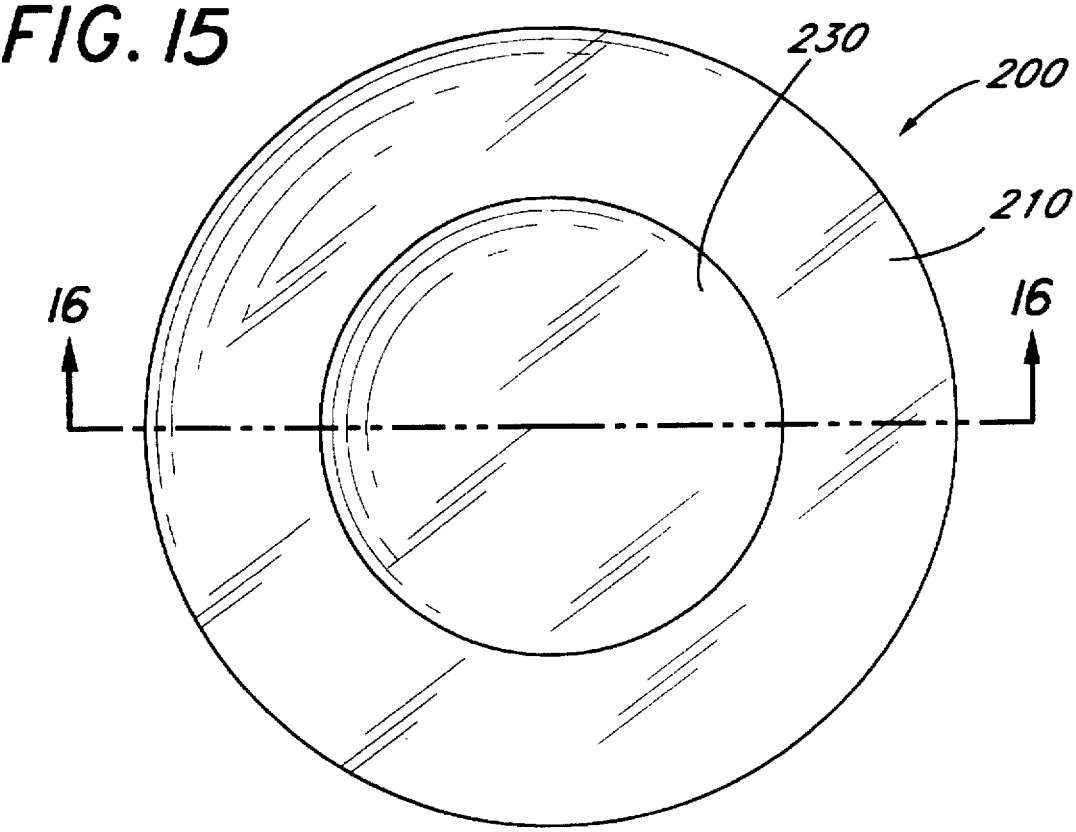
FIG. 15 is a plan view of a lens for correcting hyperopia.
Figure 16:
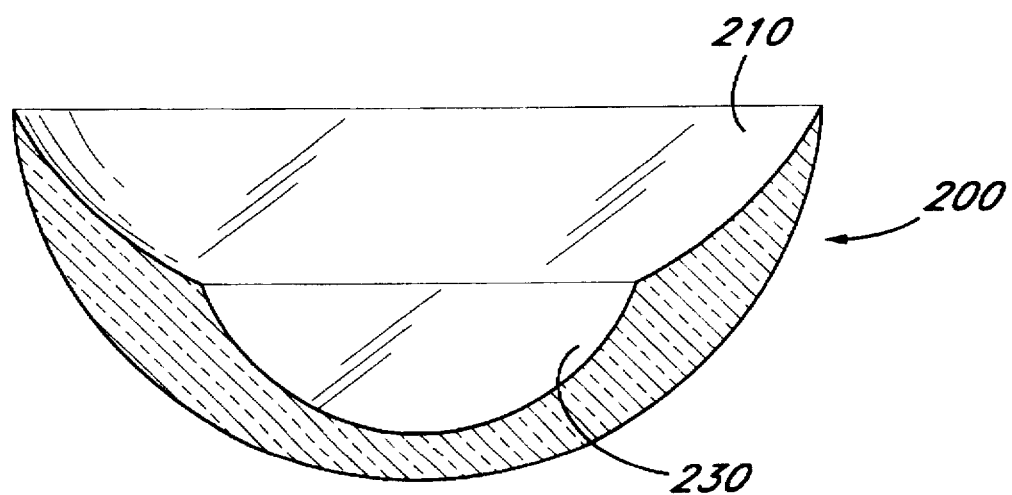
FIG. 16 is a cross-sectional view of the lens for correcting hyperopia of FIG. 15.

A further embodiment of a rigid contact lens designed specifically to be used in the treatment of hyperopia is shown in FIGS. 15 and 16. Such a contact lens should be rigid, such as the previously described lenses made from a fluoro-silicone-acrylate material. In this embodiment, the concave (posterior) portion of the lens 200 is formed with a peripheral portion 210 which has an aspheric base curve. A central portion 230 of the lens 200 is formed so that the concave surface of the central portion 230 is shaped so as to produce emmetropia. This central portion 230 has a base curve which is 2–5 diopters steeper than the base curve of the peripheral portion 210 of the lens 200, and has a radius of curvature which is up to 1 mm steeper than the peripheral portion 210. The base curve of the central portion 230 of the lens 200 may also be designed to produce a desired radius of curvature of a cornea which does not render the cornea emmotropic, but which still steepens the base curve of the cornea.

B. Myopia Enzyme-Orthokeratology Procedure

For myopia, usually there is a positively shaped cornea (steeper in the center 33 and flatter paracentrally 36). See FIG. 3A. The base curve of the contact lens 14 (FIG. 2) should usually be flatter than the central corneal curvature 33 up to the amount of the myopia in diopters. The inner radius of the intermediate zone 15 may be up to 4 diopters steeper than the base curve. The steeper central corneal curvature 33 is reshaped to a flatter curvature 37 and the flatter paracentral curvature 36 is reshaped to a steeper shape 38. The result is a spherical cornea from center to paracentral with a flatter central curvature. This eliminates myopia because the light is refracted further back on the retina (FIG. 3B) instead of in front of the retina (FIG. 3C), and there is less spherical aberration.

As will be apparent to one of skill in the art, a number of other lens designs can be used in treating myopia, which have varying diameters, base curves and thicknesses. Included in such designs are contact lenses having aspheric base curves and peripheral curves, and those having spherical base curves and aspheric peripheral curves.

The following example illustrates the method for correcting myopia using Enzyme-Orthokeratology. In this example, the patient exhibits 20/300 U.V.A. or 3 diopters myopia; a flattest central curvature of 45 diopters or 7.5 mm; and a paracentral curvature of 40 diopters and the cornea is positively shaped at +0.30. The initial rigid gas permeable contact lens (FIG. 1 and 2) contains an enzyme formula taught by this invention in its hollow chamber 11. The base curve 14 is 42 diopters or 8.0 mm (3 diopters flatter than central curvature). The optic zone 18 width is 8.0 mm. The power of the lens is plano (0). The size of the lens is 9.6 mm (8.0+1.6 mm). Its thickness is 0.20 mm. The intermediate curve 15 radius is 7.5 mm or 45 diopters (3 diopters steeper than the base curve) with a width of 0.50 mm. The peripheral curve 17 has a radius of 10.0 mm, with a width of 0.30 mm.

The lens is loaded with a dose of hyaluronidase enzyme formula (approximately 2 to 4 drops) of 500 units/μl by pressure injection through one of the holes 16 using a microscopic needle. Ultrasound may also be used to load the lens with enzyme.

The contact lens is properly fitted to the cornea and the enzyme is released into the cornea over the course of from a few minutes to a few days, as appropriate. The enzyme penetrates through the epithelium and Bowman's membrane into the stroma where it softens the mucopolysaccharide layer. The softened pliable cornea reshapes its anterior central curvature (45 diopters) to the posterior base curve 14 of the lens (42 diopters). The cornea's new anterior central curvature becomes 42 diopters (3 diopters flatter than its original 45 diopters). The paracentral anterior cornea (40 diopters) steepens to 42 diopters=8.0 mm. The cornea now has a spherical shape. The original three diopters of myopia is now reduced to no correction (plano or emmetropic) and unaided (natural) visual acuity is improved to normal 20/20 from 20/300.

The enzyme dissipates out of the cornea over the following few hours to a few days and the cornea hardens with the new shape, rendering the eye emmetropic (no correction) and leaving normal, natural vision (20/20). Inhibitors or other means of "hardening" a cornea can also be used to lock in the changes to the shape of the cornea. The final enzyme orthokeratology lens is left on the eye for a period of time necessary to establish the desired new calculated curve to correct refractive error after the cornea hardens to stabilize the corneal change and act as a retainer lens. It is then removed. New retainer contact lenses are fitted only if necessary to stabilize the new curvature over the period of a few more days, and the amount of time they must be worn everyday is reduced systematically until they are no longer worn at all. The new reformed cornea's memory system only knows the new shape so the cornea will not regress to its old shape in the absence of retainer lenses.

C. Astigmatism Enzyme-Orthokeratology Procedure

Figure 4A:
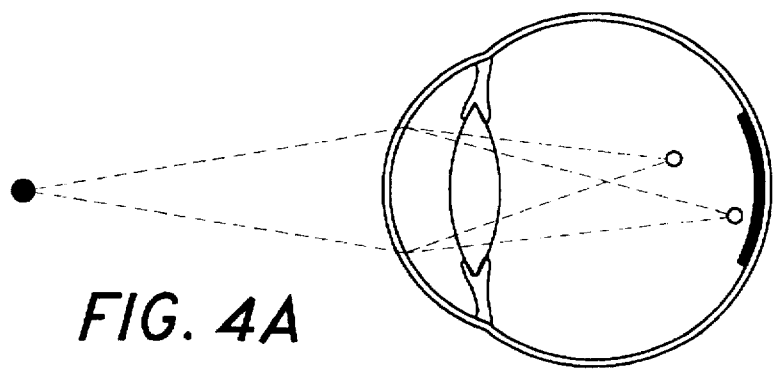
FIG. 4A is a schematic illustration of the convergence of light within the eye at more than one point, occurring in astigmatism.
Figure 4B:
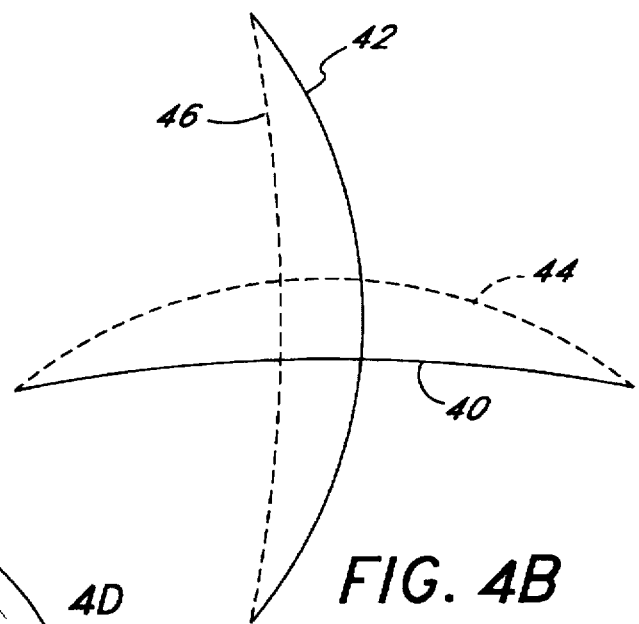
FIG. 4B illustrates the central corneal curvature in an astigmatic eye, illustrating a shorter radius of curvature within a first plane and a relatively longer radius of curvature within a second plane substantially perpendicular to the first plane.
Figure 4C:
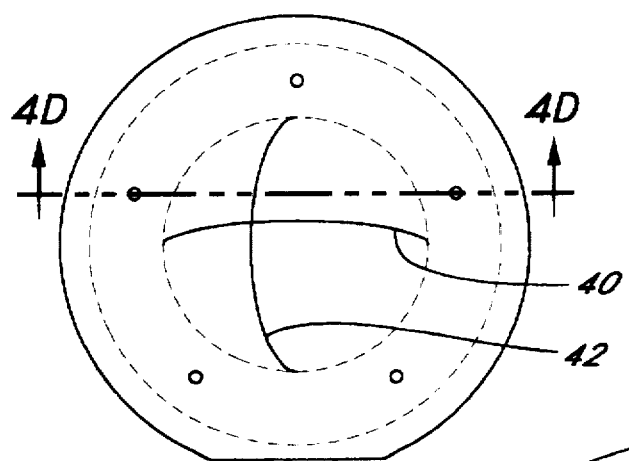
FIG. 4C is a plan view of a toric Enzyme-Orthokeratology contact lens for astigmatism.
Figure 4D:
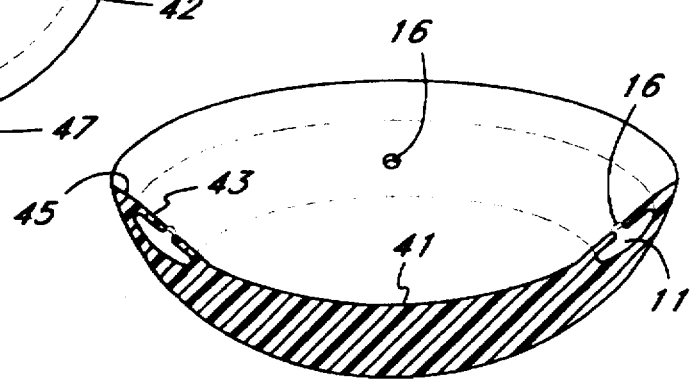
FIG. 4D is a cross-sectional view of a lens to correct astigmatism.
Figure 5A:
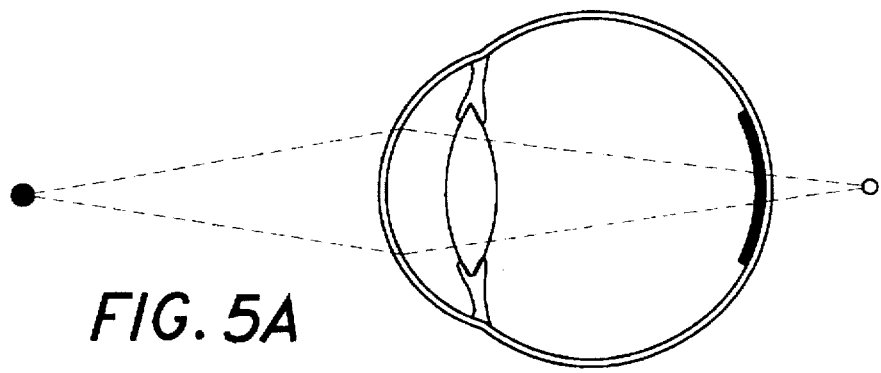
FIG. 5A illustrates the convergence of light behind the retina in the case of farsightedness (hyperopia).

For astigmatism, the central corneal curvature is uneven, which causes a stretching of the image on the retina (FIG. 4A). The horizontal and vertical central meridians are different curvatures 40, 42 (FIG. 4B). The astigmatism contact lenses may use toric and aspheric base curves 40, 42 (FIG. 4C), intermediate curves, and perilpheral curves which may incorporate prism and/or truncation 47 (FIG. 4C). The initially flatter central meridian of the eye 40 is reshaped to take on a steeper curvature 44 and the initial steeper central meridian 42 is reshaped to take on a flatter curvature 46. This process reshapes the central corneal curvature to a spherical shape and eliminates astigmatism.

To correct astigmatism using Enzyme-Orthokeratology, the following procedure may be used. In the preferred embodiment of the invention, the material for the lens is fluorosilicon-acrylate. The base curves 41 (6.0 mm–8.5 mm) may be back toric, front toric, or bitoric. The flattest central corneal curvature is aligned with a steeper base curvature. The steeper central corneal curvature is aligned with a flatter base curvature. Aspheric or spherical base curves and peripheral curves may also be used. The lens diameter is the base curve in mm+1.3 to 1.8 mm. The range is 7.5 mm to 11.5 mm. The optic zone 18 diameter equals the base curve in mm and ranges from 6.5 to 9.5 mm. The intermediate curve 43 radius ranges from 1 diopter to 2 diopters flatter than the base curve. The width is from 0.35 to 1.0 mm. The peripheral curves 45 range from 2 to 4 diopters flatter than the base curve 41. The width is 0.35 to 1.0 mm. The intermediate 43 and peripheral curves 45 may be aspheric. Prism and/or truncation 47 is used to keep the lens aligned in the proper position to reshape the astigmatic cornea.

The thickness of the lens varies with lens power. If zero lens power=0.20 mm, subtract 0.01 mm for each diopter of minus and add 0.02 mm for each diopter of plus power. The power of the lens is computed based on the patients refractive error and the base curve/corneal curvature relationship. The astigmatic lenses may incorporate the enzyme/agents in the chamber 11 as already discussed or be used without the enzyme after the cornea has been softened.

D. Hyperopia Enzyme Orthokeratology Procedure

Figure 5B:
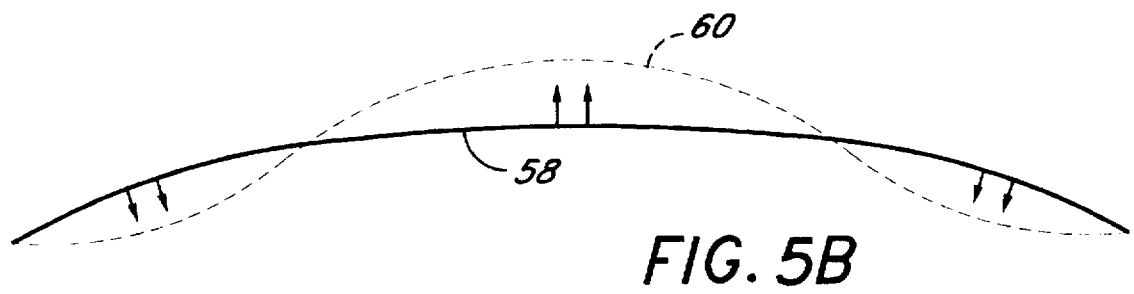
FIG. 5B illustrates the relatively flattened cornea before Enzyme-Orthokeratology in accordance with the present invention, in solid lines, and the shape of the cornea in phantom lines following the method of the present invention.

For hyperopia, the central curvature 58 of the cornea must be reshaped to a steeper curvature 60 (FIG. 5B). The light entering an eye must be refracted more because the image projected through the cornea is focusing behind the retina (FIG. 5A) needs to be moved forward onto the retina with more refraction, that is, more light bending at the cornea. The lens base curve (50 FIGS. 5C and 5D) may be fitted steeper than the central corneal curvature with flatter aspheric intermediate 52 and peripheral 54 curves. A hole 56 in the center of the lens may be used to encourage and give the space for the central cornea 51 to steepen. Alternatively, a contact lens as shown in FIGS. 15 and 16 can be used to correct hyperopia.

Figure 5C:
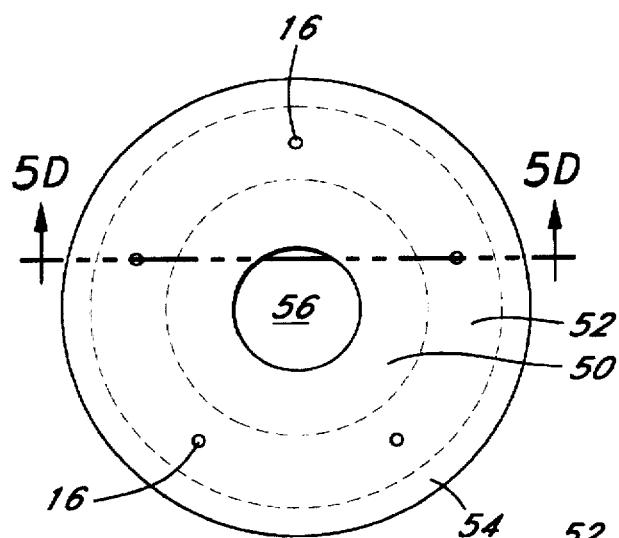
FIG. 5C is a plan view of an Enzyme-Orthokeratology contact lens for hyperopia.
Figure 5D:
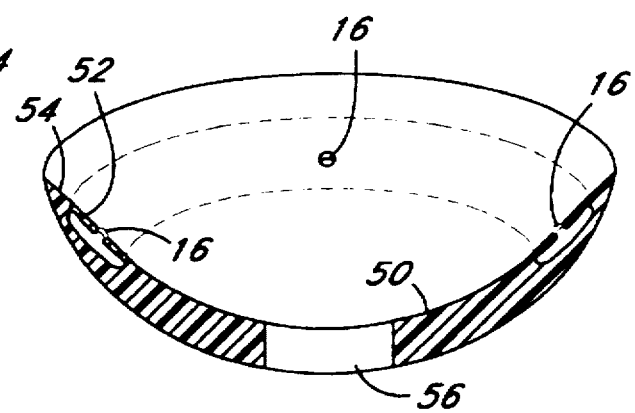
FIG. 5D is a cross-sectional view along the lines 5P–5D in FIG. 5C.
Figure 9:
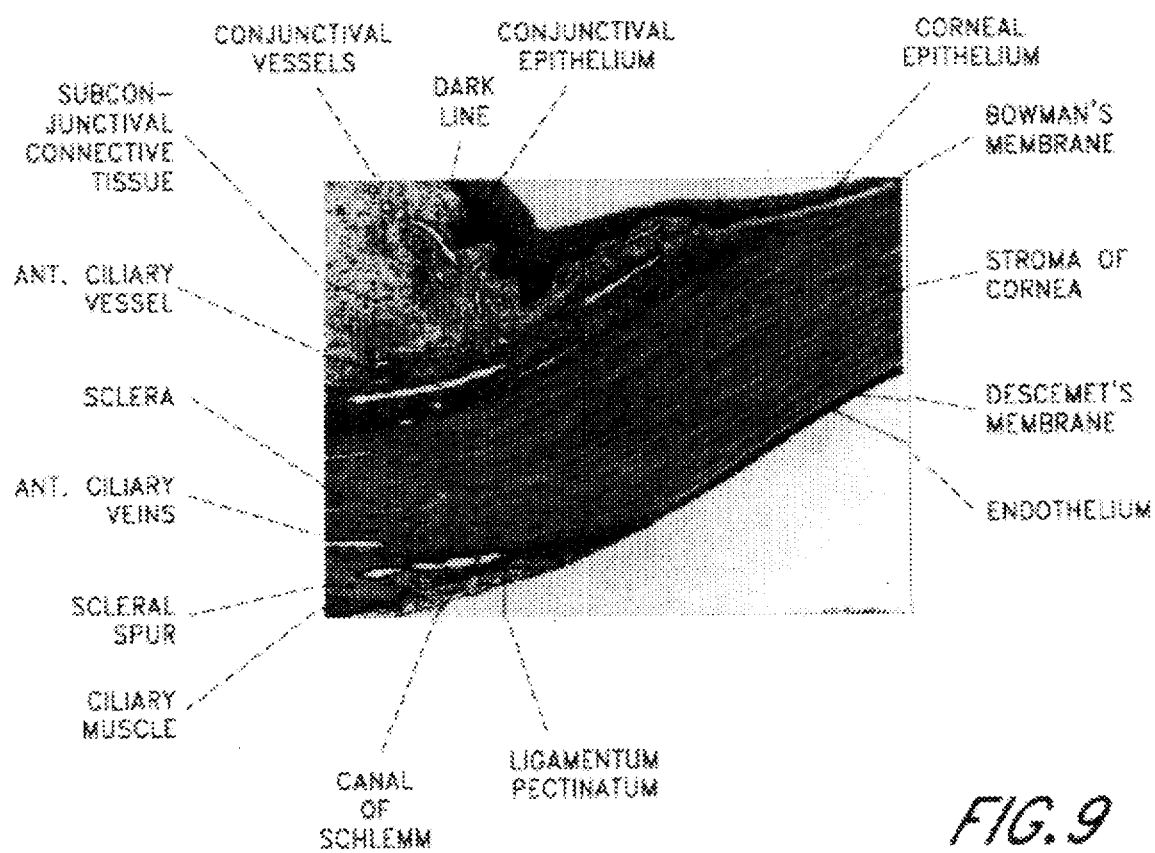
FIG. 9 is a microphotograph of a cross section of the human cornea.

To correct hyperopia using Enzyme-Orthokeratology, the following procedure can be used. In the preferred embodiment of the invention, a fluoro-silicone-acrylate material is used for the lens (FIG. 5C). A hole 56 ranging from 2.5 mm to 4.5 mm diameter is provided in the center. The base curve 50 of the lens is fit steeper than the central corneal curvature. The base curves 50 vary from 5.5 mm to 8.0 mm, and the diameter is the base curve 50 in mm+1.0 mm to 1.5 mm (6.5 to 9.5 mm range). Smaller diameters are used because the curvature of lenses is steeper than that of the central cornea. The intermediate 52 and peripheral 54 curves should be aspheric curves 1.0 to 3 diopters flatter than the base curve 50. The width of these curves is 0.35 mm to 1.0 mm. The optic zone 50, 56 is between 5.5 mm to 8.0 mm. The thickness of the lens is dependent upon the power necessary for correction. With hyperopia the lenses will be thicker. If the power is plano (0) the thickness=0.20 mm, then add 0.02 for each diopter of plus. The power of the lens is computed based on the patients refractive error adjusted for the base curve/corneal curvature relationship. The hyperopic lenses may incorporate the enzyme/agents in the chamber 11 as already discussed or be used without the enzyme after the cornea is softened.

In an alternate embodiment of the treatment of hyperopia using Enzyme-Orthokeratology, an enzyme or agent is first applied to the cornea as in the foregoing embodiments of the methods of the present invention. Once the cornea has begun to soften, the cornea is at first allowed to change shape without the use of a rigid contact lens. Due to the intraocular pressure of the eye, the radius of curvature of a cornea will naturally steepen in a regular fashion without the application of a contact lens to cause such steepening. This natural steepening of the radius of curvature of the cornea is allowed to progress until the desired radius of curvature has been achieved in the previously hyperopic cornea. At this point, the enzyme or agent used to soften the cornea is inhibited, and a rigid lens whose posterior surface has a desired radius of curvature is then applied to the softened cornea as a retainer lens until the cornea regains its structural integrity and "hardness." In this method of Enzyme-Orthokeratology, therefore, a desired corneal shape can be produced without the use of a rigid contact lens, although such a lens is desirably used after a desired shape has been reached in order to preserve that shape.

IV. Other Therapeutic Uses of Enzyme-Orthokeratology

In addition to correcting refractive errors of an otherwise normally functioning eye, the present methods of reshaping a cornea can be used to effect other therapeutic benefits as well. One contemplated therapeutic use of the present methods is to rehabilitate the irregularity of abnormal corneas and improve refractive errors which occur as a result of diseases such as keratoconus, contact lens-induced corneal warpage, or corneal manipulations such as corneal surgery, including such surgical procedures as radial keratotomy, photorefractive keratectomy, corneal transplant surgery, and cataract surgery. One of the most common reasons for the clinical failure of surgical procedures like corneal transplants, for example, is the existence of residual refractive error such as irregular astigmatism following an otherwise successful surgery. Therefore, the present methods can be used to correct the refractive error that occurs as a result of disease, surgery, or other conditions.

Improving corneal smoothness, inducing an appropriate corneal shape, and improving corneal irregularity are other therapeutic benefits of using the methods of the present invention. For example, a cornea which does not have a smooth surface can be made smoother by the application of a corneal softening agent followed by the shaping of the cornea with a mold or contact lens. Inducing appropriate corneal shape, especially in patients who have undergone surgery to the eye, such as corneal transplantation surgery, can also be accomplished with the present methods. In this way, the refractive results of such surgeries can be made more consistent, and any changes in corneal shape due to surgery can be corrected.

In order to use the foregoing methods of Enzyme-Orthokeratology, to effect these further clinical benefits, subjects who have an irregularly-shaped cornea or who have undergone a corneal manipulation are first identified. Such identification is normally accomplished by an eye specialist, who can diagnose an individual as having an irregularly shaped cornea as having undergone corneal manipulation. The previously described methods of Enzyme-Orthokeratology are then used to reshape the cornea of the individual to a desired configuration.

The following Examples illustrate embodiments of the present invention. Such Examples are illustrative only and not meant to limit the scope of the present invention.

EXAMPLE 1

Exogenous Enzyme Dosage Determination

New Zealand white rabbits are anesthetized with ketamine and xyzaline. In each rabbit, one cornea serves as a control. This cornea is exposed to saline solution only. The other cornea of each rabbit is exposed to an enzyme to be tested for its ability to produce softening of the cornea. A measured amount of a solution containing the exogenous enzyme to be tested is injected into the cornea of each rabbit. After a period of time, both corneas in each rabbit are analyzed to determine the softening effect of the enzyme tested. In order to determine softening, the results of the following tests performed on each cornea of a rabbit are compared:
(1) Pachymetry, to measure the corneal thickness;
(2) Keratometry, to measure the central corneal curvature;
(3) Computer assisted corneal topography, to evaluate surface topographical change of a cornea;
(4) Slit-lamp examination, to evaluate the clarity of the cornea, anterior chamber, and iris;
(5) Tonometry, to measure the intra-ocular pressure in the eye of each rabbit;
(6) Fundoscopic exam, to evaluate the optic nerve and retina;
(7) Retinoscopy, to measure refractive error; and
(8) Fluorescein or Rose Bengal staining, to identify damage to the corneal epithelium.

These tests are then repeated after another period of time in order to determine the duration and affects of the dosage of the enzyme which was administered.

EXAMPLE 2

Use of an Inactivator of an Inhibitor of an Endogenous Enzyme

Approximately 0.25 grams of iodoacetamide is dissolved in 100 ml of isotonic saline in order to produce a solution of 0.25% iodoacetamide. Approximately 1–2 drops of this solution is applied every hour for 4 hours to the subject.

EXAMPLE 3

Use of an Enzyme Inhibitor

The inhibitor EDTA (ethylene diamine tetracetic acid) is dissolved in isotonic saline to produce a solution of approximately 0.01% EDTA. Approximately 1–2 drops of the solution are applied 2–3 times per day. This treatment is continued for several days in order to stop the softening reactions of enzymes in the cornea which break down proteoglycan or collagen components of the cornea.

The drawings, parameters, constants, and concentrations set forth in this patent disclosure are given as examples and are in no way final, binding, or limiting. As many changes could be made in the above constructions and methods without departing from the scope of the invention, it is intended that all matter contained in the above description or shown in the accompanying drawings shall be interpreted as illustrative and not in a limiting sense.

What is claimed is:

1. A method of correcting refractive errors in an eye of a subject mammal, comprising the steps of:

selecting an agent which is a proteolytic enzyme on the basis of its being able to soften the cornea in said eye of said subject without causing damage to said cornea;

administering to said subject a corneal softening amount of said enzyme so that said cornea can be reshaped from a first configuration to a desired second configuration;

fitting said cornea with a rigid contact lens having a concave curvature of said desired second configuration;

permitting said cornea to reshape to said desired second configuration under the influence of said lens; and removing said lens when said cornea is capable of maintaining said desired second configuration without the support of said lens.

2. The method of claim 1, wherein said enzyme is an enzyme which breaks down collagen in said cornea.

3. The method of claim 2, wherein said enzyme is selected from the group consisting of matrix metalloproteinase-1 and matrix metalloproteinase-2.

4. The method of claim 1, wherein said agent is administered in combination with proparacaine hydrochloride.

5. The method of claim 1, wherein said agent is administered in the form of eye drops.

6. The method of claim 5, wherein said eye drops include liposomes which contain said agent.

7. The method of claim 1, wherein said agent is administered to said cornea by means of iontophoresis.

8. The method of claim 1, wherein said rigid contact lens carries an amount of said agent sufficient to soften said cornea, said agent being administered to said eye by means of said rigid contact lens.

9. The method of claim 8, wherein said rigid contact lens comprises a chamber between the anterior and posterior surfaces thereof and a hole in the posterior surface thereof, and wherein said agent is released from said chamber and through said hole.

10. The method of claim 9, wherein a series of rigid contact lenses containing said agent in said chamber are successively fitted to the cornea, the central concave radius of the posterior surface of each successive lens being progressively more similar to that of a desired corneal configuration.

11. The method of claim 9, wherein said contact lens is constructed from two layers laminated to each other, wherein a chamber for holding fluid is formed between said two layers when the contacting surfaces of said two layers are laminated together, and wherein the posterior layer of said contact lens has at least one hole for delivering fluid from said chamber to said eye.

12. The method of claim 1, wherein the central concave radius of said contact lens is equal to the convex radius required by said cornea to render said eye emmetropic.

13. The method of claim 1, wherein said enzyme is administered by injecting said enzyme directly into the corneal stroma from a side of said eye.

14. The method of claim 1, wherein said enzyme is administered by injecting said enzyme anteriorly through the epithelium of said eye.

15. The method of claim 1, additionally comprising fitting a soft contact lens which comprises a material that is impregnated with said agent before fitting said rigid contact lens.

16. The method of claim 15, wherein said material comprises collagen.

17. A method of reshaping a cornea from a first configuration to a second desired configuration in order to correct refractive errors in an eye of a subject mammal, comprising the steps of:

providing a soft contact lens;

selecting an agent which is a proteolytic enzyme in the basis of its being able to soften the cornea in said eye of said subject, without causing damage to said cornea;

loading said soft contact lens with an amount of said agent sufficient to soften the cornea in said eye;

fitting said soft contact lens to said cornea, said corneal softening agent in said soft contact lens thereafter causing said cornea to become softer and more pliable;

removing said soft contact lens; and fitting at least one rigid contact lens to said cornea while said cornea is in the softened condition, thereby causing said cornea to reshape to the configuration of the concave curvature of said rigid contact lens.

18. The method of claim 17, wherein said soft contact lens comprises a hydrophilic material.

19. The method of claim 18, wherein said material is collagen.

20. The method of claim 17, wherein said soft contact lens is loaded with said corneal softening agent by soaking said soft contact lens in a solution of said agent.

21. The method of claim 17, wherein a rigid retainer contact lens is fitted on top of said soft contact lens while said soft contact lens is on said cornea to maintain the shape of said cornea during the softening process.

22. The method of claim 21, wherein said soft contact lens is bonded to said rigid retainer contact lens.

23. A method of correcting refractive errors in an eye of a subject mammal, comprising the steps of:

providing a combination contact lens having a rigid center and a soft annular skirt extending beyond the outer perimeter of said rigid center, said rigid center having a paracentral curvature sufficient to render an eye of said subject mammal emmetropic;

selecting an agent which is a proteolytic enzyme on the basis of its being able to soften the cornea in said eve of said subject without causing damage to said cornea;

loading said annular skirt with an amount of said agent sufficient to soften the cornea of said eye;

releasing said cornea softening agent into said cornea, thereby softening said cornea and making it more pliable, said cornea then reshaping to the posterior curvature of the rigid center of said combination lens and rendering said eye emmetropic.

24. A method of correcting refractive errors in an eye of a subject mammal, comprising the steps of:

(a) providing a contact lens for delivering agents to said eye, said contact lens comprising:

a rigid anterior layer;

a rigid posterior layer having a convex side and a concave side, wherein the convex side of said posterior layer has a flatter curvature than the concave side of said anterior layer over a center portion of said posterior layer; and a channel in said center portion of said poster layer, wherein said channel passes from the convex side of said posterior layer to the concave side of said posterior layer, wherein the concave side of said anterior layer and the convex side of said posterior layer are joined, thereby forming a center chamber between said layers in communication with the concave side of said posterior layer by means of said channel;

(b) selecting an agent which is a proteolytic enzyme on the basis of its being able to soften the cornea in said eye of said subject without causing damage to said cornea;

(c) loading said center chamber of said contact lens portion with an amount of said agent sufficient to soften the cornea of said eye; and (d) releasing said corneal softening agent into said cornea from said central chamber, thereby softening said cornea and making it more pliable, said cornea then reshaping to the inside central curvature of said posterior layer of said contact lens.

25. A method of correcting refractive errors in an eye of a subject mammal, comprising the steps of:

(a) providing a contact lens for delivering agents to said eye, said contact lens comprising:

a rigid anterior layer having a posterior surface with an intermediate portion;

a rigid posterior layer having an interior surface with an intermediate portion, wherein the intermediate portion of the posterior surface of said anterior layer has a steeper radius of curvature than the anterior surface of the intermediate portion of said posterior layer; and a channel in said intermediate portion of said posterior layer wherein said channel passes from the convex side of said posterior layer to the concave side of said posterior layer, wherein the concave side of said anterior layer and the convex side of said posterior layer are joined, thereby forming a peripheral chamber between said layers in said intermediate portions, and wherein said channel is in communication with both said peripheral chamber and the posterior surface of said posterior layer of said contact lens;

(b) selecting an agent which is a proteolytic enzyme on the basis of its being able to soften the cornea in said eye of said subject without causing damage to said cornea;

(c) loading said peripheral chamber of said contact lens with an amount of said agent sufficient to soften the cornea of said eye; and (d) releasing said corneal softening agent into said cornea from said central chamber, thereby softening said cornea and making it more pliable, said cornea then reshaping to the inside central curvature of said posterior layer.

26. A method of rehabilitating corneal irregularity and correcting refractive error in an eye of a subject mammal with irregular corneal shape, comprising the steps of:

identifying a subject with irregular corneal shape;

selecting a proteolytic enzyme on the basis of its being able to soften the cornea in said eye of said subject without causing damage to said cornea;

administering to said subject a corneal softening amount of said enzyme so that said cornea can be reshaped from a first configuration to a desired second configuration;

fitting said cornea with a contact lens having a concave curvature of said desired second configuration;

permitting said cornea to reshape to said desired second configuration under the influence of said lens; and removing said lens when said cornea is capable of maintaining said desired second configuration without the support of said lens.

27. The method of claim 26, wherein said subject is identified by diagnosing said subject as having a condition selected from the group consisting of: keratoconus, contact lens induced corneal warpage, and irregular corneal shape or uncorrected refractive error due to corneal surgery.

28. A method of improving the clinical success of surgery to the eye involving the manipulation of a cornea of a subject mammal, comprising the steps of:

identifying a subject who has undergone a corneal manipulation;

selecting an agent which is a proteolytic enzyme on the basis of its being able to soften the manipulated cornea of said subject without causing damage to said cornea;

administering to said subject a corneal softening amount of said enzyme so that said cornea can be reshaped from a first configuration to a desired second configuration;

fitting said cornea with a contact lens having a concave curvature of said desired second configuration;

permitting said cornea to reshape to said desired second configuration under the influence of said lens; and removing said lens when said cornea is capable of maintaining said desired second configuration without the support of said lens.

29. The method of claim 28, wherein said corneal manipulation is selected from the group consisting of radial keratotomy, corneal transplant surgery, cataract surgery, and corneal reshaping by laser.

* * * * *

UNITED STATES PATENT AND TRADEMARK OFFICE
CERTIFICATE OF CORRECTION

PATENT NO. : 5,788,957
DATED : August 4, 1998
INVENTOR(S) : Donald H. Harris

It is certified that error appears in the above-identified patent and that said Letters Patent is hereby corrected as shown below:

at Column 27, line 46, the word "eve" should be corrected to reflect the word "eye";
at Column 28, line 61, the phrase "selecting a proteolytic enzyme" should be corrected to reflect the phrase, "selecting an agent which is a proteolytic enzyme".

Signed and Sealed this

Seventeenth Day of April, 2001

*Attest:*

NICHOLAS P. GODICI

*Attesting Officer*      Acting Director of the United States Patent and Trademark Office